US011143637B2

(12) United States Patent
Lee et al.

(10) Patent No.: US 11,143,637 B2
(45) Date of Patent: Oct. 12, 2021

(54) RAPID ANALYSIS AND IDENTIFICATION OF LIPIDS FROM LIQUID CHROMATOGRAPHY-MASS SPECTROMETRY (LC-MS) DATA

(71) Applicant: AGENCY FOR SCIENCE, TECHNOLOGY AND RESEARCH, Singapore (SG)

(72) Inventors: Dong-Yup Lee, Singapore (SG); Hock Chuan Yeo, Singapore (SG); Ying Swan Ho, Singapore (SG); Shuwen Chen, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 11 days.

(21) Appl. No.: 16/634,962

(22) PCT Filed: Aug. 7, 2018

(86) PCT No.: PCT/SG2018/050402
§ 371 (c)(1),
(2) Date: Jan. 29, 2020

(87) PCT Pub. No.: WO2019/032049
PCT Pub. Date: Feb. 14, 2019

(65) Prior Publication Data
US 2020/0240964 A1 Jul. 30, 2020

(30) Foreign Application Priority Data
Aug. 7, 2017 (SG) .......................... 10201706416R

(51) Int. Cl.
H01J 49/04 (2006.01)
G01N 30/72 (2006.01)
(Continued)

(52) U.S. Cl.
CPC ...... *G01N 30/7233* (2013.01); *H01J 49/0045* (2013.01); *H01J 49/0431* (2013.01); *G01N 2030/027* (2013.01)

(58) Field of Classification Search
CPC .......... G01N 30/7233; G01N 2030/027; H01J 49/0045; H01J 49/0431
See application file for complete search history.

(56) References Cited

U.S. PATENT DOCUMENTS

2002/0172961 A1* 11/2002 Schneider ............ C12Q 1/6872
435/6.12
2003/0068825 A1* 4/2003 Washburn .......... G01N 33/6851
436/86

(Continued)

OTHER PUBLICATIONS

Yeo et al., "A Genetic Algorithm-based Approach for Pre-processing Metabolomics and Lipidomics LC-MS Data", Metabolomics, vol. 12, No. 1, Nov. 9, 2015, 13 pages.

(Continued)

Primary Examiner — David J Bolduc
(74) Attorney, Agent, or Firm — Marshall, Gerstein & Borun LLP

(57) ABSTRACT

The present invention generally relates to a method for analyzing and identification of the plurality of lipids in a sample that is profiled using a combined Liquid Chromatography-Mass Spectrometry (LC-MS) technique, comprising the steps of:
a) providing a list of Liquid Chromatography-Mass Spectrometry (LC-MS)-based mass features;
b) deconvoluting said list of LC-MS-based mass features;
c) inferring daughter ions from the deconvoluted list of LC-MS-based mass features;
d) identifying one or more parental exact masses from the inferred daughter ions;
e) scoring each of the one more parental exact masses based on the inferred daughter ions;

(Continued)

f) determining characteristic mass features in response to the scoring of each of the one or more parental exact masses; and g) determining each of the plurality of lipids based on the characteristic mass features thereof.

In particular, the present invention also relates to identification of the plurality of lipids undergoing in-source fragmentation.

24 Claims, 14 Drawing Sheets

(51) Int. Cl.
*H01J 49/00* (2006.01)
*G01N 30/02* (2006.01)

(56) References Cited

U.S. PATENT DOCUMENTS

| | | | | |
|---|---|---|---|---|
| 2004/0108452 | A1* | 6/2004 | Graber | H01J 49/0027 250/281 |
| 2005/0040326 | A1* | 2/2005 | Enke | H01J 49/0045 250/288 |
| 2006/0226082 | A1* | 10/2006 | Brook | G01N 30/50 210/656 |
| 2006/0287834 | A1* | 12/2006 | Kearney | G01N 33/6848 702/27 |
| 2007/0218505 | A1* | 9/2007 | Kearney | G01N 33/6848 435/7.1 |
| 2008/0070314 | A1* | 3/2008 | Geromanos | G16B 15/00 436/86 |
| 2010/0219335 | A1* | 9/2010 | Bardotti | G01N 30/7233 250/282 |
| 2011/0121172 | A1* | 5/2011 | Savitski | H01J 49/0045 250/282 |
| 2013/0206979 | A1* | 8/2013 | Bonner | G16C 20/90 250/282 |
| 2013/0280742 | A1* | 10/2013 | Young | G01N 30/78 435/23 |
| 2014/0051113 | A1* | 2/2014 | Stephenson, Jr. | H01J 49/0036 435/34 |
| 2014/0330524 | A1* | 11/2014 | Geromanos | G01N 30/7206 702/19 |
| 2015/0170892 | A1* | 6/2015 | Geromanos | G01N 30/8631 702/28 |
| 2015/0293058 | A1* | 10/2015 | Wuhr | G01N 33/68 436/173 |
| 2017/0047209 | A1* | 2/2017 | Bailey | H01J 49/0036 |
| 2017/0345635 | A1* | 11/2017 | Makarov | H01J 49/40 |
| 2018/0024132 | A1* | 1/2018 | Kiebish | G01N 33/57434 435/7.23 |
| 2018/0143169 | A1* | 5/2018 | Astarita | G01N 33/50 |
| 2018/0224406 | A1* | 8/2018 | Xuan | H01J 49/0081 |
| 2018/0340174 | A1* | 11/2018 | Lundorf | C12N 15/1034 |
| 2018/0350576 | A1* | 12/2018 | Giannakopulos | H01J 49/10 |
| 2018/0350578 | A1* | 12/2018 | Yip | H01J 49/005 |
| 2020/0234938 | A1* | 7/2020 | Kibbey | G01N 27/622 |
| 2020/0381231 | A1* | 12/2020 | Bailey | G01N 33/6848 |

OTHER PUBLICATIONS

Ni et al., "LipidHunter Identifies Phospholipids by High-Throughput Processing of LC-MS and Shotgun Lipidomics Datasets", Analytical Chemistry, vol. 89, No. 17, Jul. 28, 2017, pp. 8800-8807.

Lim et al., "Computational Approach to Structural Identification of Phospholipids Using Raw Mass Spectra From Nanoflow Liquid Chromatography-electrospray Ionization-tandem Mass Spectrometry", Journal of Mass Spectrometry, vol. 47, No. 8, Aug. 8, 2012, pp. 1004-1014.

Lee et al., "Precursor Mass Prediction by Clustering Ionization Products in LC-MS-based Metabolomics", Metabolomics, vol. 9, No. 6, Apr. 21, 2013, pp. 1301-1310.

Lynn et al., "Metabolite Identification for Mass Spectrometry-based Metabolomics Using Multiple Types of Correlated Ion Information", Analytical Chemistry, vol. 87, No. 4, Dec. 28, 2014, pp. 2143-2151.

Tsugawa et al., "MS-DIAL: Data-independent MS/MS Deconvolution for Comprehensive Metabolome Analysis", Nature Methods, vol. 12, No. 6, May 4, 2015, pp. 523-526.

Search Report in International Application No. PCT/SG2018/050402 dated Nov. 19, 2018, 2 pages.

* cited by examiner

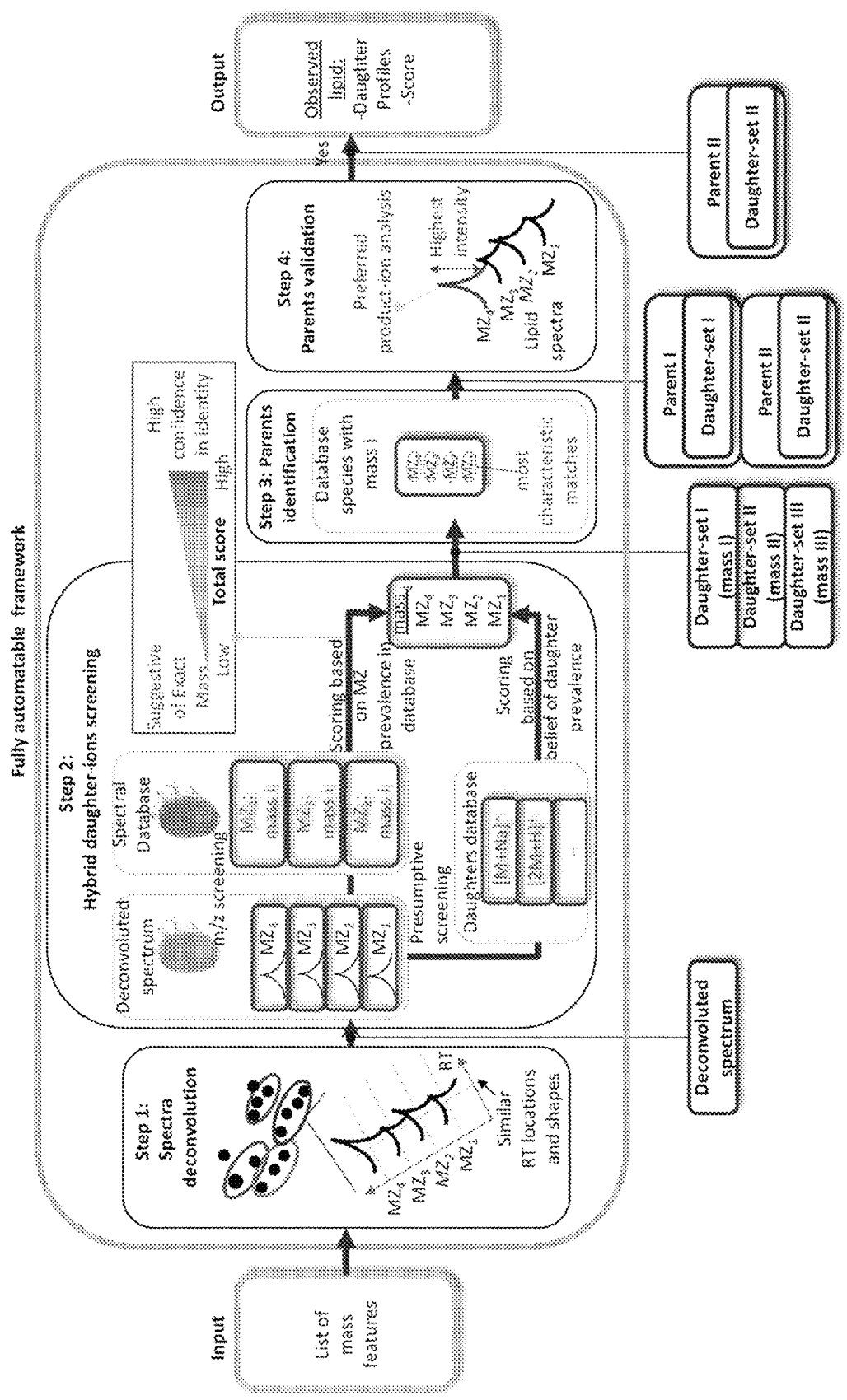
[Fig. 1]

[Fig. 2a]
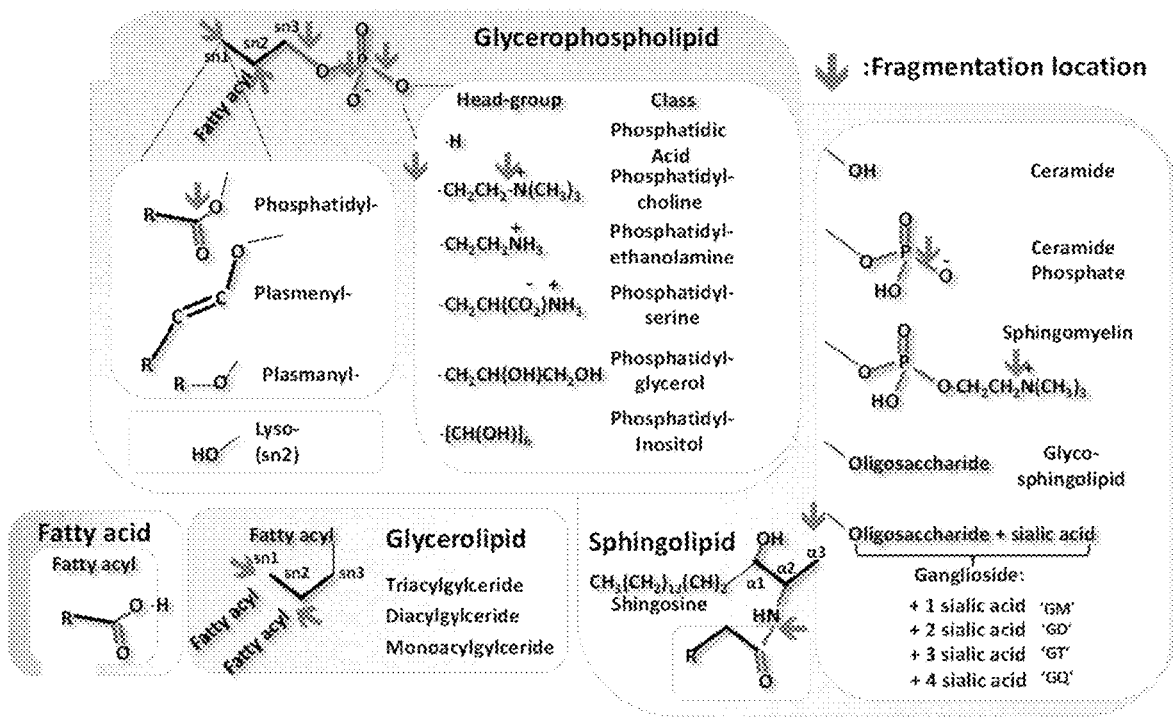
[Fig. 2b]
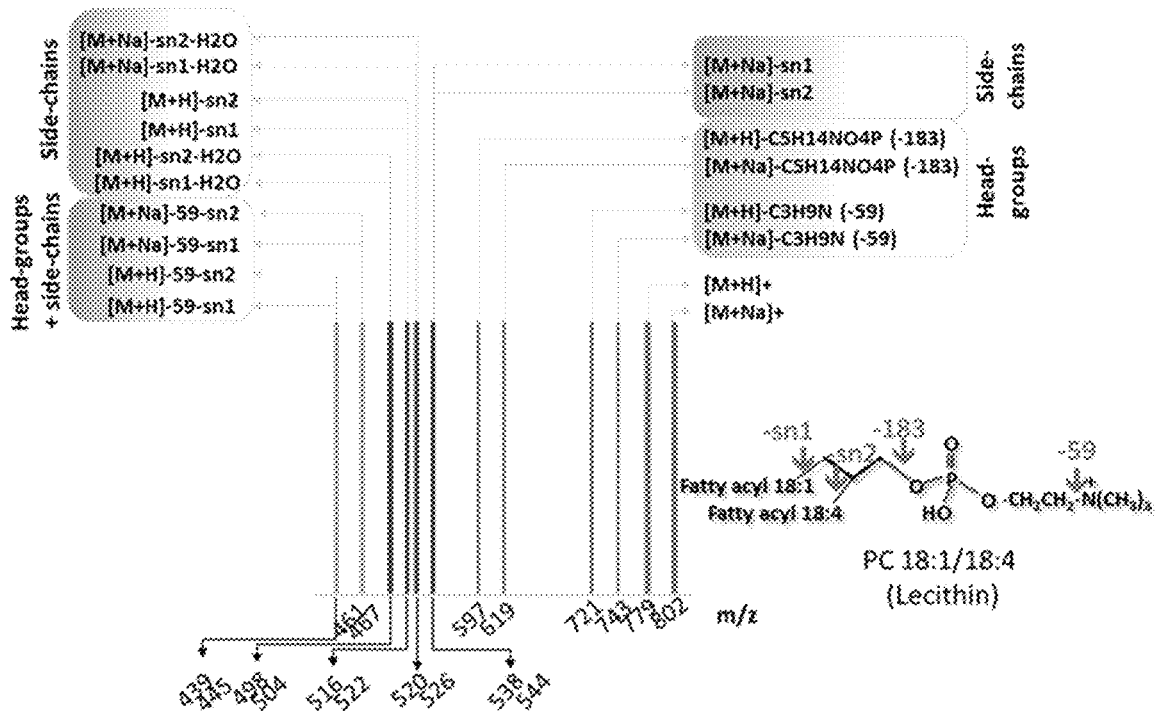

[Fig. 3]
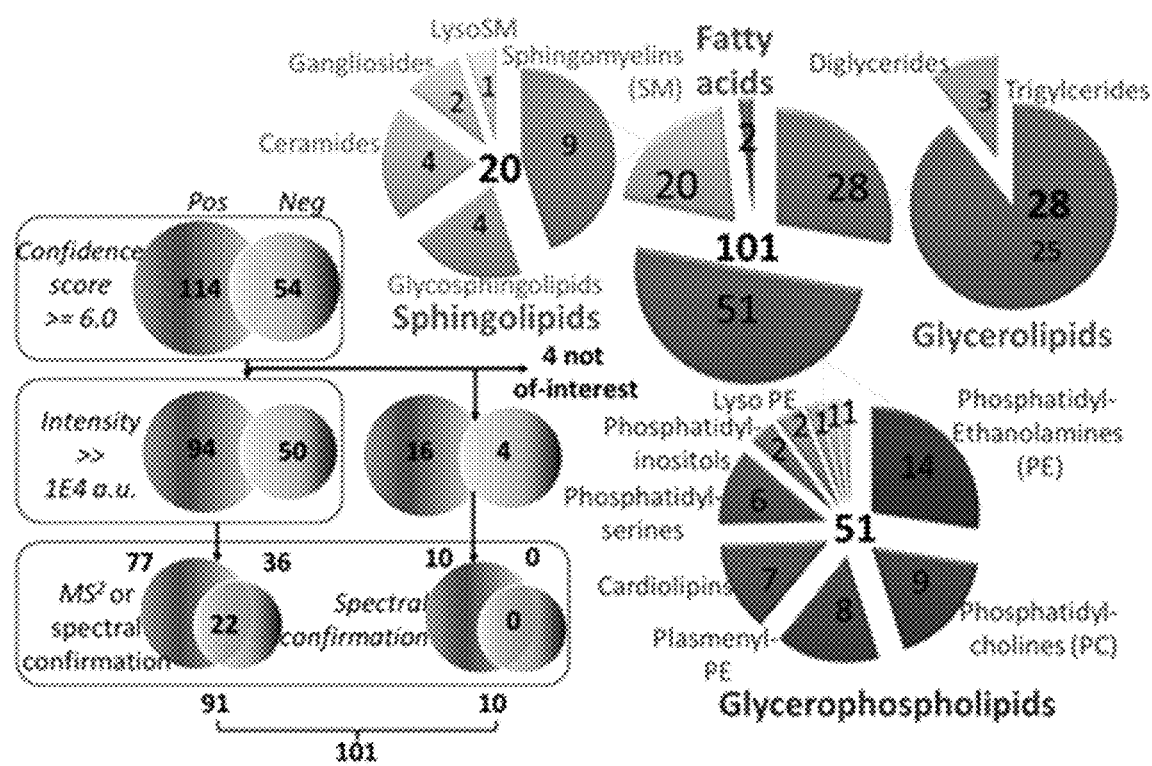

[Fig. 4a]
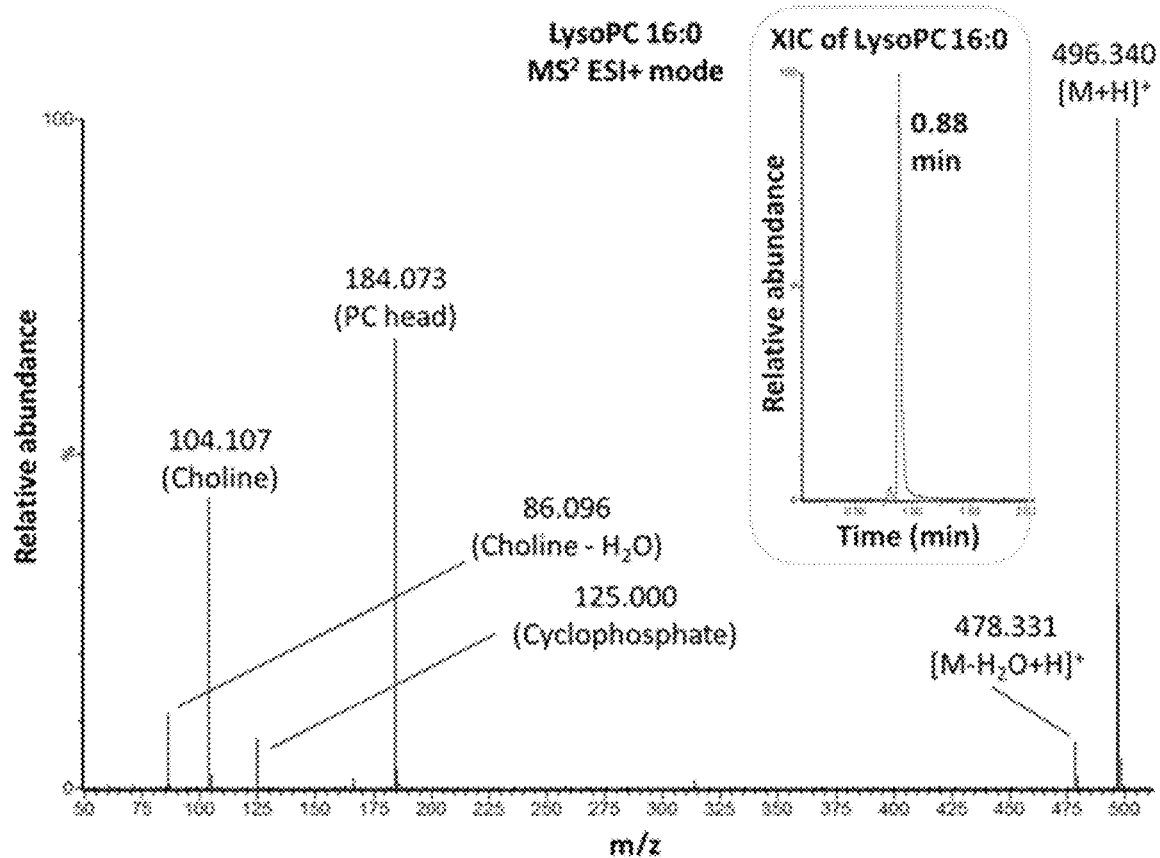

[Fig. 4b]
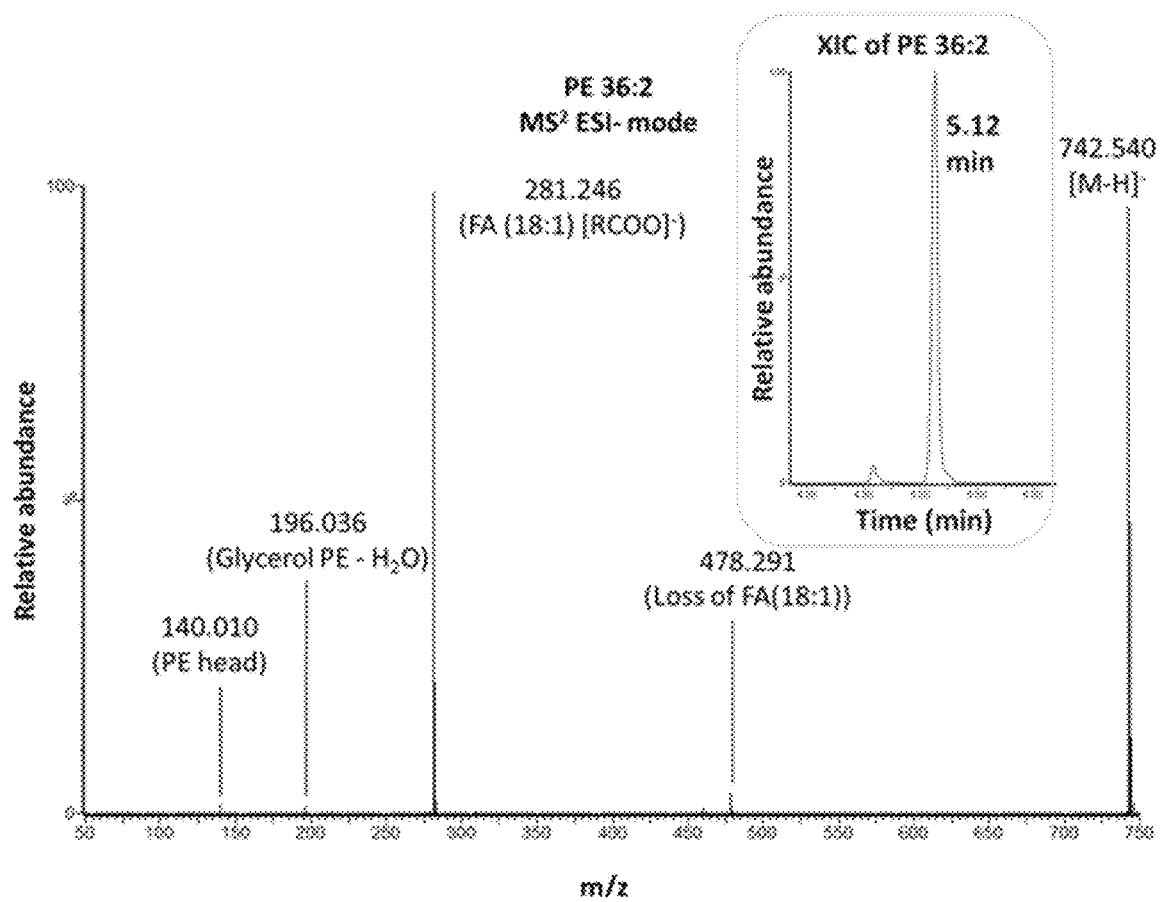

[Fig. 5]
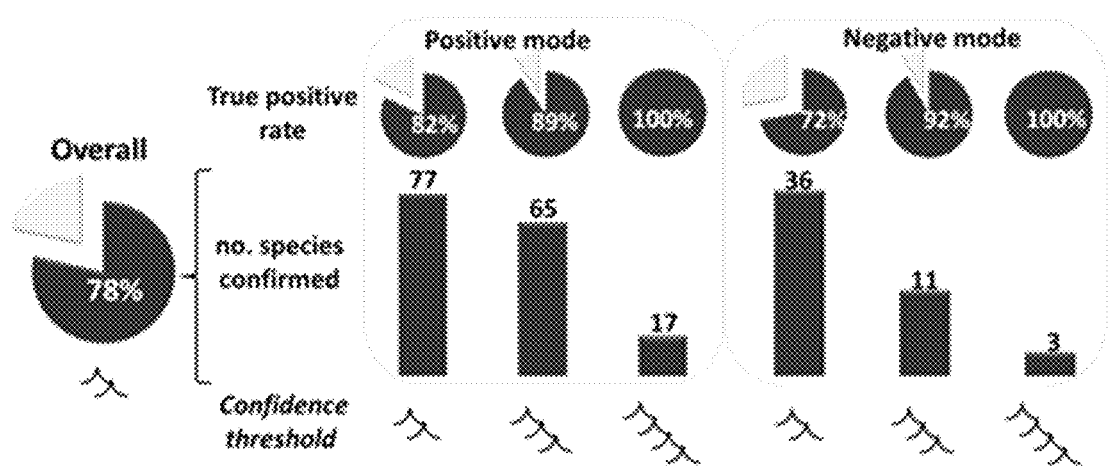

[Fig. 6]
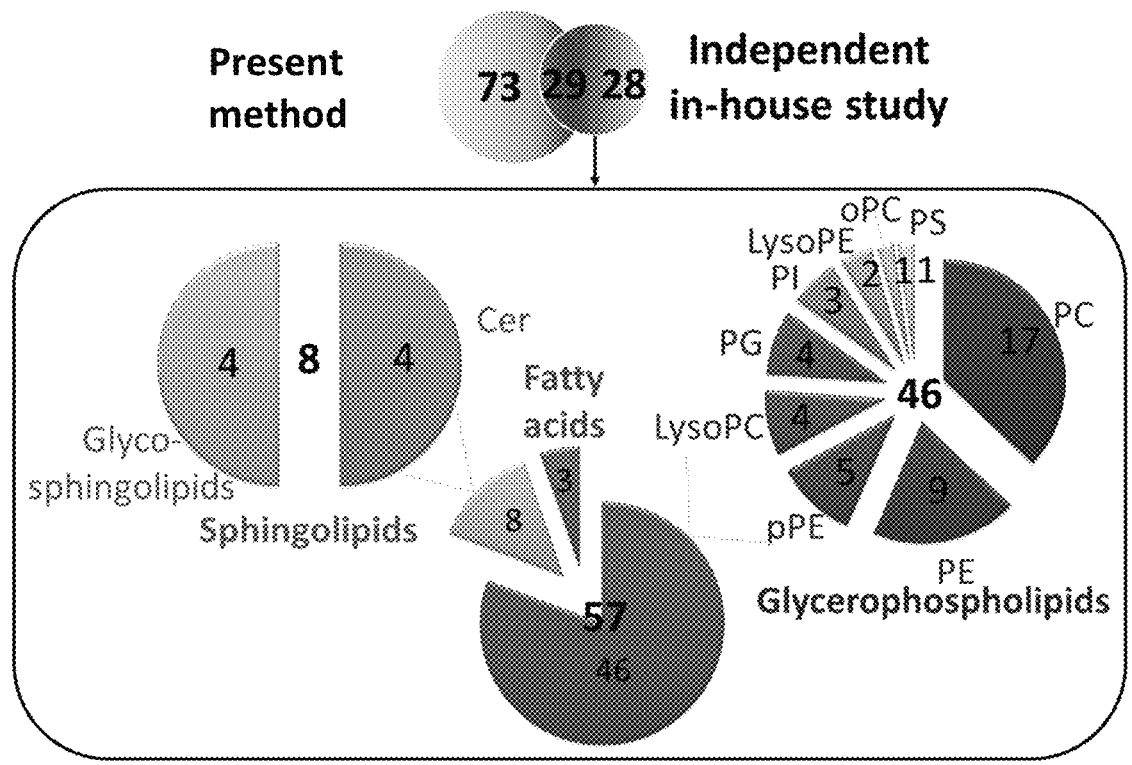

[Fig. 7]
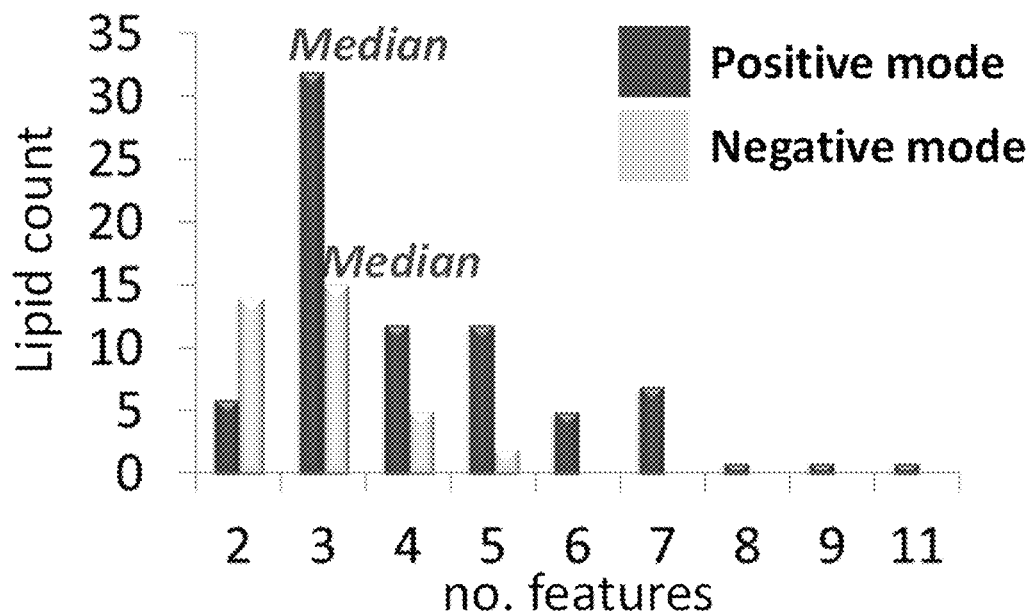
[Fig. 8]
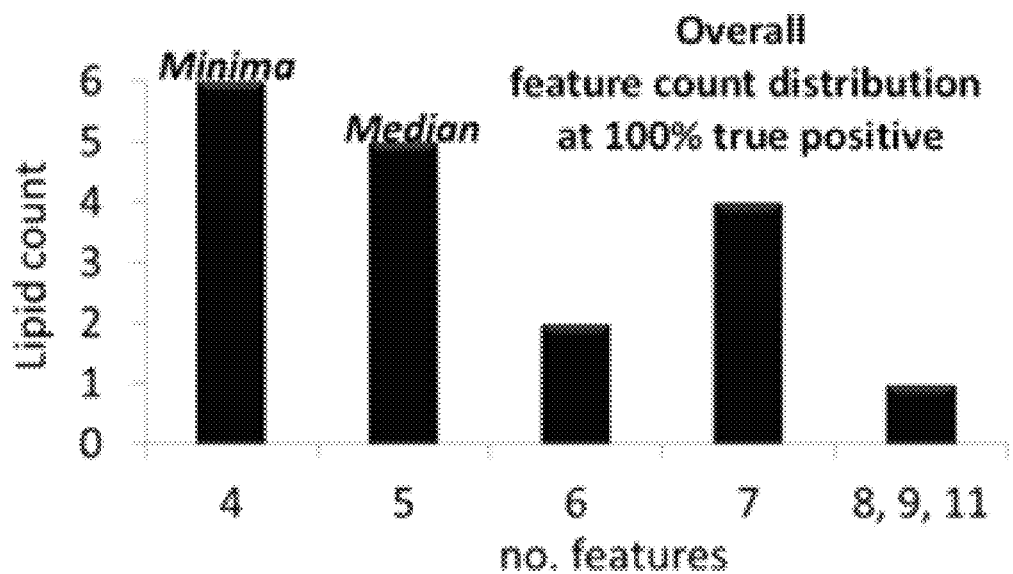

[Fig. 9]
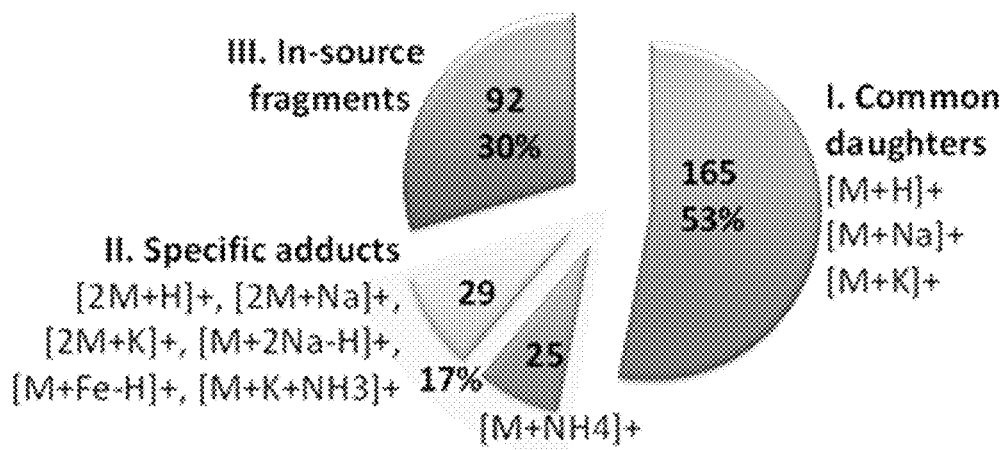
[Fig. 10]
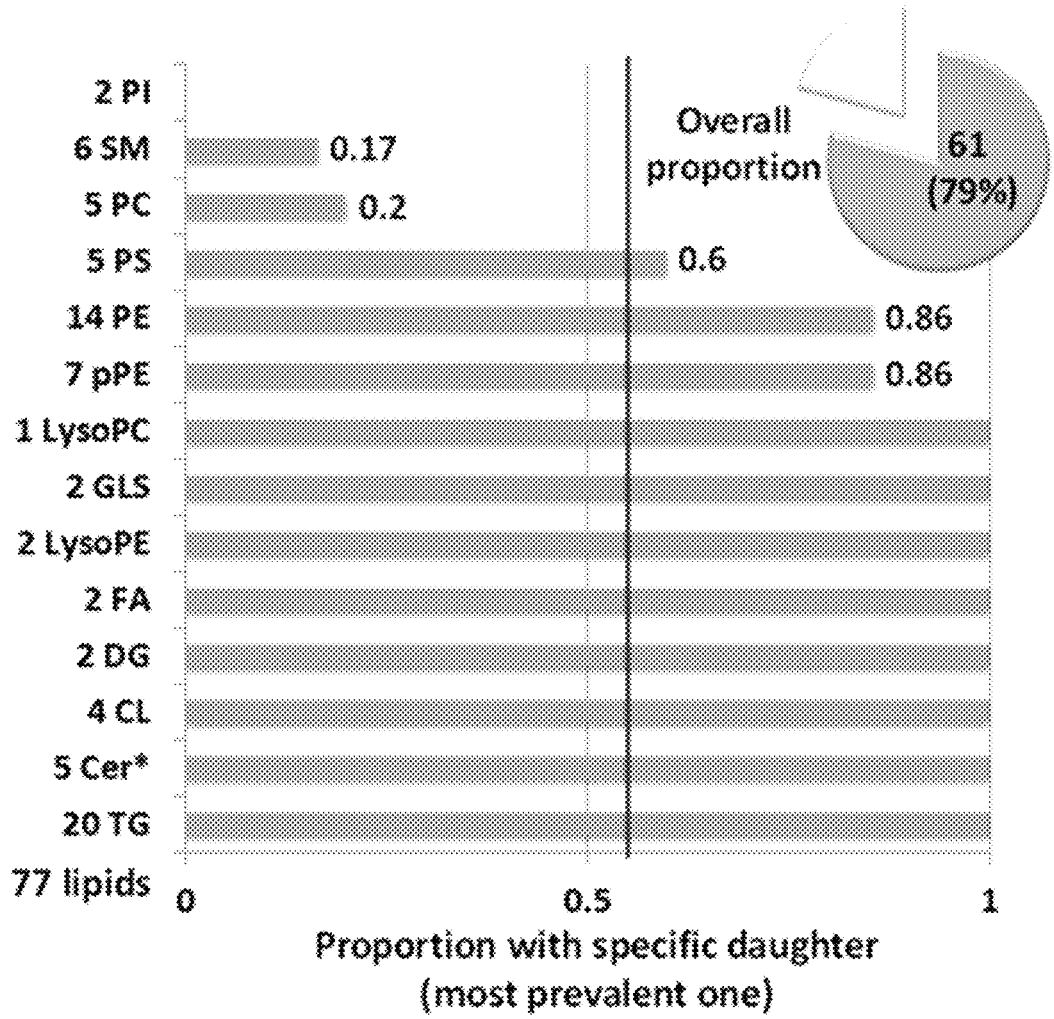

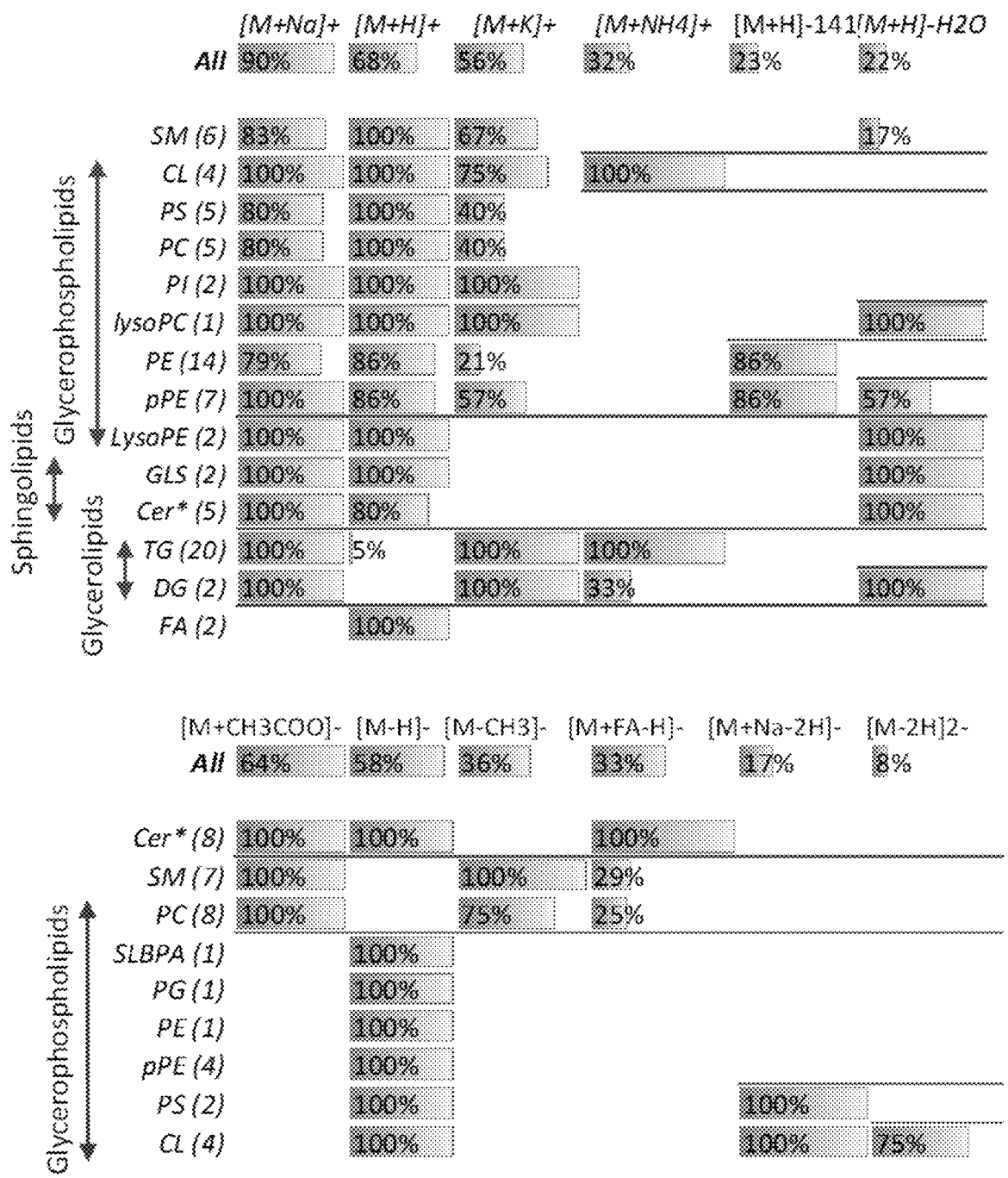
[Fig. 11]

[Fig. 12]
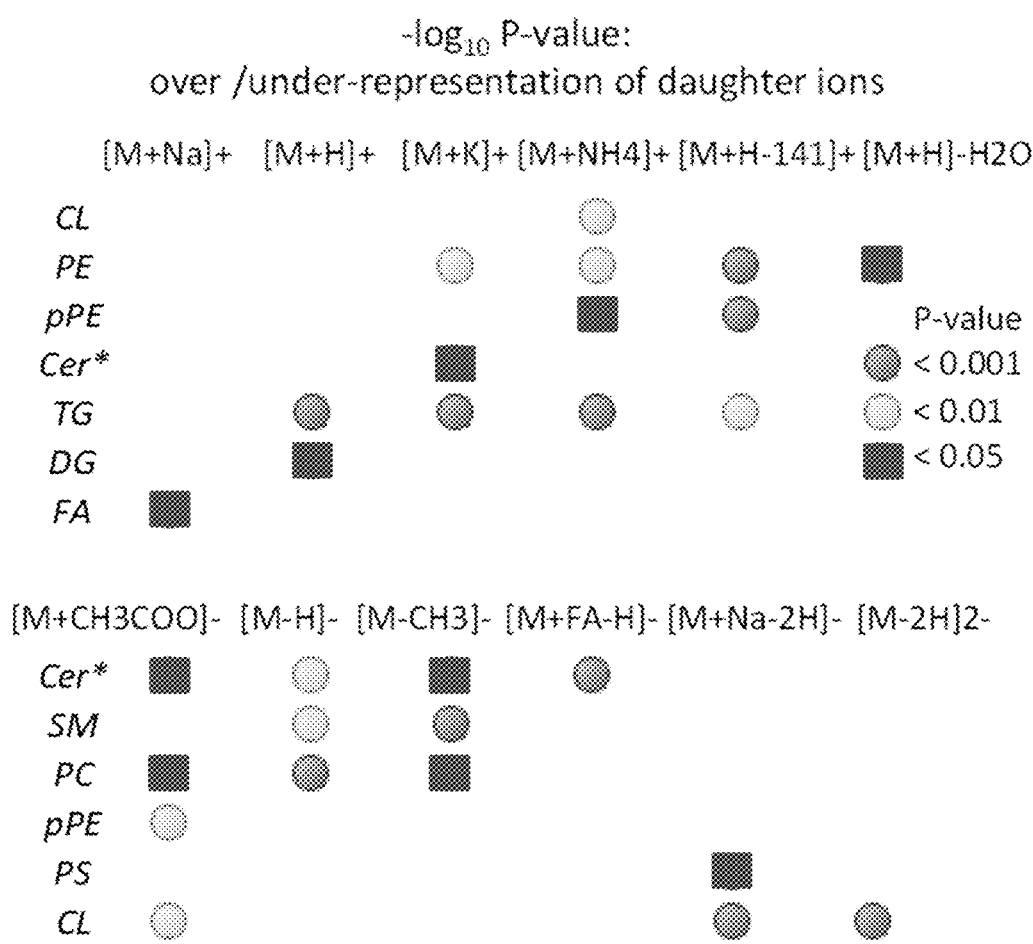

[Fig. 13]
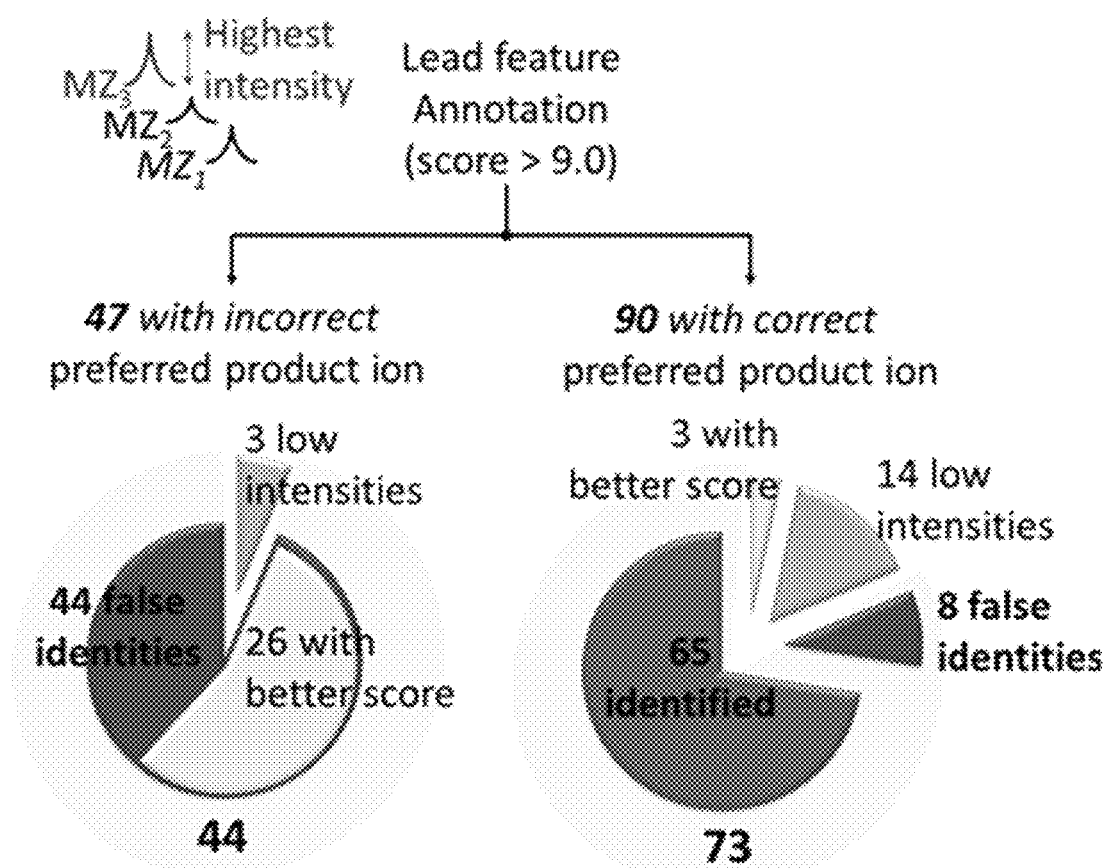

[Fig. 14]
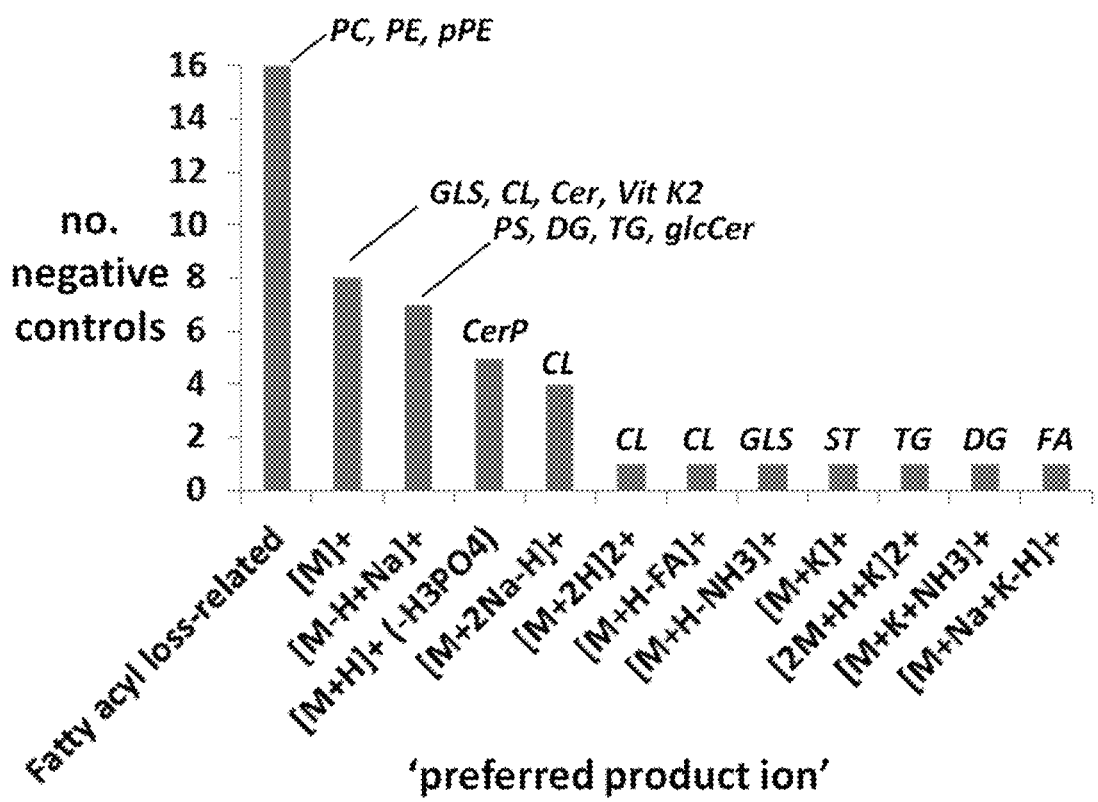

[Fig. 15]
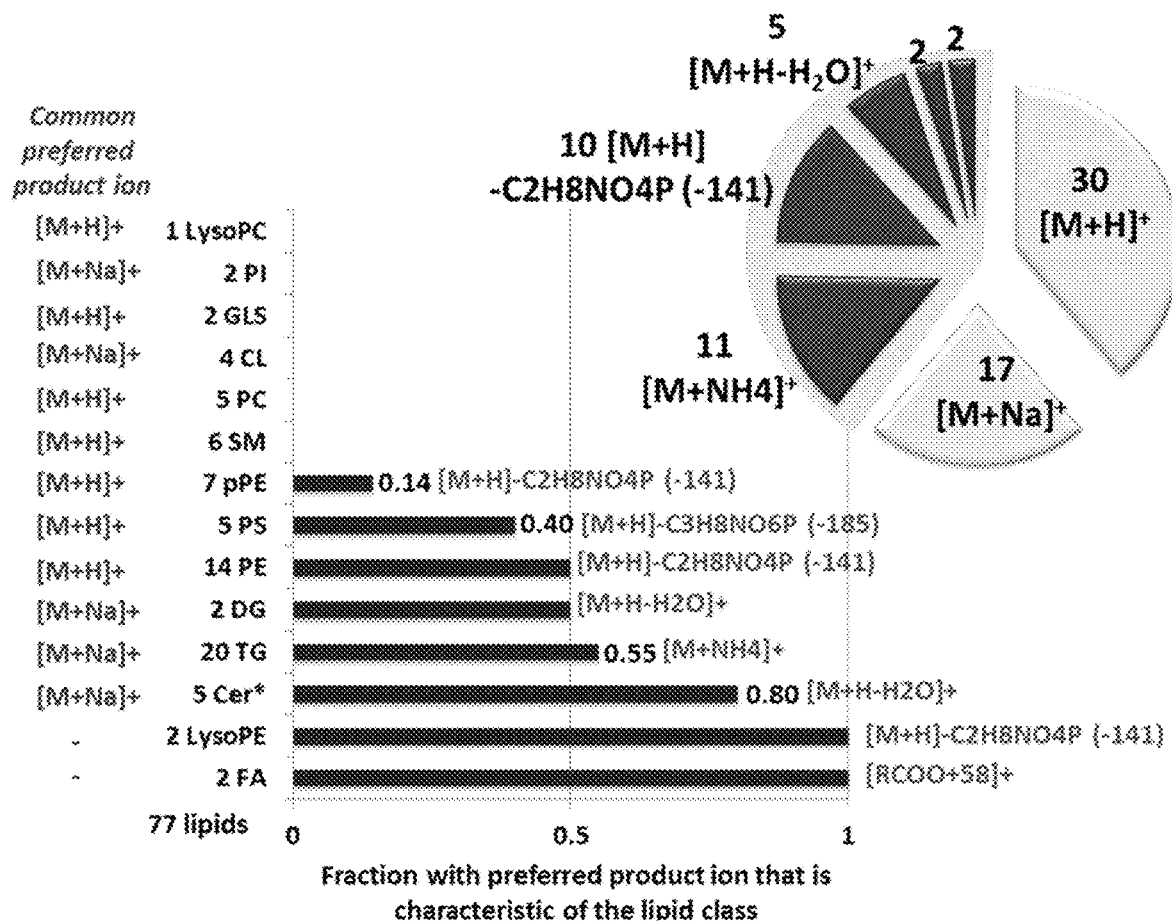

RAPID ANALYSIS AND IDENTIFICATION OF LIPIDS FROM LIQUID CHROMATOGRAPHY-MASS SPECTROMETRY (LC-MS) DATA

REFERENCES TO RELATED APPLICATIONS

The present application claims the benefit of Singapore Application No. 10201706416R, filed on 7 Aug. 2017, and incorporated herein by reference.

TECHNICAL FIELD

The present invention generally relates to a method for analyzing and identification of the plurality of lipids. In particular, the present invention also relates to identification of the plurality of lipids undergoing in-source fragmentation.

BACKGROUND ART

Lipids are generally identified using combined liquid chromatography-mass spectroscopy (LC-MS) techniques due to their wide coverage in terms of molecular weight, ease of sample preparation and tunable column chemistry and mobile phases. From a LC-MS experiment, the primary data obtained are the mass-to-charge (m/z) ratio, intensity, and retention time (RT) of detected mass features representing products of MS ionization. Once the same features in various samples are determined, the approach for identifying their underlying metabolites is to first recover parental masses based on the best practices of daughter-ion inference, while taking into account the isotopic relations. The associated metabolites are then identified by way of matching predicted masses to available databases including Kyoto Encyclopaedia of Genes and Genomes (KEGG), Human Metabolome Database (HMDB) and LIPID MAPS structure database.

In order to reduce the number of false candidates, information of the daughter ions is often pooled and then analysed collectively by either clustering or graphical approaches. To do so effectively, a genetic algorithm-based method has been introduced. This method eases the optimization of the related parameters, concurrently for pathways-of-interest and untargeted metabolites. More importantly, by relieving customization burden from the user, it is likely to enable an efficient pre-processing of highly complex datasets that are tailored to specified objectives.

Regardless of the approaches adopted, it would be necessary to validate the analysis using independent evidence to determine the lipid identity. The leads of the lipids identified during the analysis may be verified by virtue of spectral comparison with databases or standards, or elucidating the structural details more exhaustively, which typically involves the use of tandem mass spectroscopy ($MS^2$) technique. During $MS^2$ validation, ions-of-interest are selected from the first stage of MS based on m/z values, for fragmentation by collision-induced dissociations. The resulting product-ions are then profiled in the second MS stage to confirm the structure of suspect molecules. Other examples of related technologies used for verification include 'information-dependent acquisition' (IDA), 'simultaneous acquisition of exact mass at high and low collision energy' (MSE) and 'sequential window acquisition of all theoretical fragment ion spectra' (SWATH) analysis.

However, the LC-MS-based methods are generally exploratory in nature without established method for prioritizing good leads while maintaining false ones at low level. Therefore, the further selection of candidates is highly dependent on the user's experience, expertise and ad-hoc knowledge; thus, workflows are typically biased with compromised effectiveness. As an example, the characteristic RT of parent species can be used as a post-hoc filter to improve confidence in their identifications. Yet the RT, rigorously measured using standard, is not available for the vast number of system-specific metabolites.

Notwithstanding the statistical and machine-learning methods available for inferring the values for poorly-characterized compounds, the results are only relevant for similar experimental conditions and molecular classes, yet with limited reliability. Further, the RT is still subjected to substantial 'drift' after prolonged LC column usage. In addition, RT filtering does not resolve the disadvantage of exploratory identifications which demands active intervention. Unless the system-of-interest has been perfectly characterized, the analysis will remain constrained in efficacy with such a framework.

The present invention therefore provides an alternative method to analyse and identify lipids that overcomes, or at least ameliorates, one or more of the disadvantages described above.

SUMMARY

In one aspect, there is provided method of identifying a plurality of lipids in a sample that is profiled using a combined Liquid Chromatography-Mass Spectrometry (LC-MS) technique, comprising the steps of:

a) providing a list of Liquid Chromatography-Mass Spectrometry (LC-MS)-based mass features;

b) deconvoluting said list of LC-MS-based mass features;

c) inferring daughter ions from the deconvoluted list of LC-MS-based mass features;

d) identifying one or more parental exact masses from the inferred daughter ions;

e) scoring each of the one more parental exact masses based on the inferred daughter ions;

f) determining characteristic mass features in response to the scoring of each of the one or more parental exact masses; and g) determining each of the plurality of lipids based on the characteristic mass features thereof.

In another aspect, there is provided use of the method as defined herein to identify a plurality of lipids undergoing in-source fragmentation.

Definitions

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

The following detailed description is merely exemplary in nature and is not intended to limit the invention or the application and uses of the invention. Furthermore, there is no intention to be bound by any theory presented in the preceding background of the invention or the following detailed description. It is the intent of the present embodiment to present a method of analysing and identifying a plurality of lipids in a sample that is profiled using a combined Liquid Chromatography-Mass Spectrometry (LC-MS) technique. Methods in accordance with the present embodiment comprise, among others, the steps of a) providing a list of Liquid Chromatography-Mass Spectrometry (LC-MS)-based mass features; b) deconvoluting the list of LC-MS-based mass features; c) inferring daughter ions from the deconvoluted list of LC-MS-based mass features; d) identifying one or more parental exact masses from the inferred daughter ions; e) scoring each of the one more parental exact masses based on the inferred daughter ions; f) determining characteristic mass features in response to the scoring of each of the one or more parental exact masses; and g) determining each of the plurality of lipids based on the characteristic mass features thereof.

Lipids are naturally-occurring, relatively small hydrophobic molecules that are soluble in organic solvents. There are a total of eight families of lipids classified based on distinctive 'head' and 'backbone' structures, and functions. Within each lineage, individual species are further differentiated by their side-chains according to number, length, and intra-chain positions and number of double bonds. There are also other transient modifications in response to cellular perturbation and stimulus, resulting in oxidation, hydrolysis, nitrosylation or phosphorylation. The exact global repertoire of lipids ('lipidome') further varies with nutrient availability, organism and cell-type. As such, their estimated numbers can be from thousands to millions of species depending on considerations.

The structural variability of lipids across and even within families, has served well in enabling their customization and adaptation to diverse physiological processes and many have acquired multiple, highly sophisticated functions. Their major roles include serving as energy stores, signalling molecules and structural components that are involved in metabolism, survival, proliferation, differentiation, self-renewal and immunity. However, in order to elucidate emergent phenomena in a systematic and comprehensive manner, an appropriate lipidomics framework is required to determine the repertoire, with their relative quantities, in a high-throughput, robust and accurate manner. In this regard, the expansive structural regularity of lipids, as indicated by their classification system, provides ample opportunities for concise identification in spite of their large number.

Lipids are commonly identified using liquid chromatography-mass spectroscopy (LC-MS) techniques, due to its wide coverage in terms of molecular weight, ease of sample preparation as well as tunable column chemistry and mobile phases. From experiment, the primary data obtained are the mass-to-charge (m/z) ratio, intensity, and retention time (RT) of detected mass features representing products of MS ionization. After determining the same features in various samples, the basic approach for identifying their underlying metabolites is to first recover parental masses based on the best practices of daughter-ion inference, while considering isotopic relations. The associated metabolites are then identified by matching predicted masses to available databases such as KEGG, HMDB and LIPID MAPS.

To reduce the large number of spurious candidates, daughter information are often grouped and then analysed collectively by either clustering or graphical approaches. In order to do so effectively, a genetic algorithm-based method has been introduced. Such method facilitates in optimizing the related parameters, concurrently for pathways-of-interest and untargeted metabolites. More importantly, by relieving customization burdens from the user, it enables the efficient pre-processing of highly complex datasets that are tailored to specified objectives.

Regardless of approaches, it is imperative to leverage additionally on independent evidence to determine lipid identity unequivocally. The leads of the lipids may be verified by spectral comparison with databases or standards, or elucidation of structural details more exhaustively with the usage of tandem mass spectroscopy ($MS^2$) technique. During $MS^2$ validation, ions-of-interest are selected from the first stage of MS based on m/z values, for fragmentation by collision-induced dissociations. The resulting product-ions are then profiled in the second MS stage to confirm the structure of suspect molecules. Other examples of related technologies used for verification include 'information-dependent acquisition' (IDA) analysis, 'simultaneous acquisition of exact mass at high and low collision energy' (MSE) analysis and 'sequential window acquisition of all theoretical fragment ion spectra' (SWATH) analysis.

However, there are major caveats in the way the molecules-of-interest are identified. Typical LC-MS-based methods are exploratory in nature with no established method for prioritizing good leads while maintaining false ones at low level. Consequently, the further selection of candidates is necessarily and highly dependent on a user's experience, expertise and ad-hoc knowledge; thus, workflows are typically biased with compromised effectiveness. As a case in point, the characteristic RT of parent species is used as a post-hoc filter to improve confidence in the parent species identifications. However, the RT, rigorously measured using a standard, is simply not available for a vast number of system-specific metabolites.

Despite statistical and machine-learning methods available for inferring the values for poorly-characterized compounds, the results are only relevant for similar experimental conditions and molecular classes and then even with only limited reliability. Furthermore, the RT is still subjected to substantial 'drift' after prolonged LC column usage. In addition, RT filtering does not resolve the shortcomings of exploratory identifications which demands active intervention. Unless the system-of-interest has been perfectly characterized, any analysis will remain constrained in efficacy with such a framework.

Exemplary, non-limiting embodiments of a method of identifying a plurality of lipids in a sample that is profiled using a combined Liquid Chromatography-Mass Spectrometry (LC-MS) technique, will now be disclosed.

The disclosure provides a method of identifying a plurality of lipids in a sample in accordance with the present embodiments that is profiled using a combined Liquid Chromatography-Mass Spectrometry (LC-MS) technique, comprising the steps of:

a) providing a list of Liquid Chromatography-Mass Spectrometry (LC-MS)-based mass features;

b) deconvoluting said list of LC-MS-based mass features;

c) inferring daughter ions from the deconvoluted list of LC-MS-based mass features;

d) identifying one or more parental exact masses from the inferred daughter ions;

e) scoring each of the one more parental exact masses based on the inferred daughter ions;

f) determining characteristic mass features in response to the scoring of each of the one or more parental exact masses; and g) determining each of the plurality of lipids based on the characteristic mass features thereof.

Advantageously, the method above may offer high accuracy and coverage in the analysis and identification of the plurality of lipids.

Yet advantageously, the method disclosed herein may be useful for identifying a fuller spectrum of distinctive daughters, for each lipid class that may not be exploited by methods known in the art. Therefore, the method described herein may advantageously be used to identify untargeted new species from major lipid classes.

The method as defined above may further comprise the step of validating the inferred daughter ions and/or the plurality of lipids. Therefore, the method of identifying a plurality of lipids in a sample that is profiled using a combined Liquid Chromatography-Mass Spectrometry (LC-MS) technique above may comprise the steps of:

a) providing a list of Liquid Chromatography-Mass Spectrometry (LC-MS)-based mass features;

b) deconvoluting said list of LC-MS-based mass features;

c) inferring daughter ions from the deconvoluted list of LC-MS-based mass features and optionally validating the inferred daughter ions;

d) identifying one or more parental exact masses from the inferred daughter ions;

e) scoring each of the one more parental exact masses based on the inferred daughter ions;

f) determining characteristic mass features in response to the scoring of each of the one or more parental exact masses; and g) determining each of the plurality of lipids based on the characteristic mass features thereof and optionally validating each of the plurality of lipids.

In an embodiment, step b) of the method as defined herein may comprise deconvoluting intensity mass features comprising high intensity mass features, low intensity mass features or combinations thereof in the list of LC-MS based mass features. Therefore, advantageously, by separating these features into groups, each arising from the same lipid specie, the method of the present invention may be able to significantly reduce false identification of the plurality of lipids. Such false lipid identification may be a false positive, false negative or combinations thereof. As used herein, the term "false positive" refers to an error in data reporting in which the result of the analysis incorrectly indicates the presence of one or more lipids (the result is positive), when in reality they are not present, while "false negative" refers to an error in which the result of the analysis erroneously indicates the absence of one or more lipids (the result is negative), when in fact, they are present in the sample.

Further advantageously, step c) of the method as defined above may comprise inferring common daughter ions, specific daughter ions or combinations thereof. Both common daughter ions and specific daughter ions may be independently classified as dominant and non-dominant daughter ions.

Non limiting examples of common daughter ions, when a positive mode acquisition is used, include $[M+Na]^+$, $[M+K]^+$, and $[M+H]^+$ adducts with M being a metabolite, in this instant, a lipid. When a negative mode acquisition mode is used, $[M+CH_3COO]^-$, $[M-H]^-$ and $[M+FA-H]^-$ may be the common daughter ions, with FA being formic acid [HCOOH].

Non-limiting examples of specific daughter ions include $[M+NH4]^+$ adducts (specific for Triglyceride, abbreviated as TG), $[M+H]—C_2H_8NO_4P$ fragments (specific for phosphatidylethanolamine or PE, plasmenylphosphatidylethanolamine or pPE and lysoPE), $[M+H]—(C_2N\ H_5+H_2O)$ fragments (specific for lysoPE), $[M+H/Na]—C_3H_8NO_6P$ fragments (specific for Phosphatidylserine, abbreviated as PS), $[RCOO+58]^+$ adducts (specific for fatty acid, abbreviated as FA), $[M+H-H_2O]^+$ adducts (specific for Sphingolipid, Monoglyceride or MG and Diglyceride DG) with M being a metabolite, in this instant, a lipid.

The method described herein may account for an ion annotation for the preferred modes of ionization (i.e. highest intensity) for each lipid class to verify plausible parent predictions. Accordingly, to implement the knowledge-driven analysis, a user may only require an in-source fragment database (LipidBlast as most comprehensive and freely-available proxy), additional specific adduct database, if and as when available, and a small list of preferred ions for each lipid class. The latter may be attributed to 'soft' electrospray ionization (ESI).

To provide a list of the LC-MS-based mass features as described in step a) of the method above, a sample comprising the plurality of lipids may be subjected to a LC-MS measurement using a suitable LC-MS instrument. Prior to introducing said sample into the LC-MS instrument, the sample may undergo a preparation procedure known in the art. Further, a chromatography column of the LC-MS instrument may be subjected to a pre-conditioning and cleaning steps. Once introduced into said instrument, the plurality of lipids may be eluted at different retention times (RTs) using an optimized method. Lipids that have been eluted separately, are then ionized using electron spray ionization (ESI), with the mass-to-charge ratio (m/z) of ions determined by Quadrupole Time-of-flight (Q-TOF) or Orbitrap-based Mass Spectrometer.

The step of deconvoluting the list of LC-MS-based mass features in the above method [i.e. step b)] may comprise the steps of:

b1) providing quality control (QC) samples at regular intervals;

b2) providing a model of intensity drift based on the LC-MS-based mass features in the QC samples; and b3) correcting the intensity mass features of said list of LC-MS-based mass features using the model of step b2).

In an embodiment, said QC samples above may be pooled from all samples comprising the plurality of lipids in equal portions and mixed, or the QC samples may be obtained commercially as a mixture of standard lipids. Hence, said QC sample may be considered as a representative of the sample type being analyzed.

In a further embodiment, the model in step b2) above may be obtained by performing a regression procedure on the LC-MS-based mass features, in particular the intensity, of QC samples. Known and suitable regression procedures may be used including a linear regression, a non-linear regression, a 'LOcal regrESSion' (LOESS), or combinations thereof. The best procedure that results in a minimal least-square error may be used, while the optimal LOESS span may be based on a leave-one-out-cross-validation approach known in the art.

In another embodiment, the intensity mass features of the list of LC-MS-based mass features may be corrected by a drift amount, obtained from the said model in step b1.2), and therefore this step may account for variations due to fluctuations including chromatography injection volumes and/or changes in conditions such as temperature and electrical circuitry during batch-run, which may result in higher reproducibility of the analysis and identification of the plurality of lipids.

In an embodiment, deconvoluting the list of LC-MS-based mass features may comprise reconstructing individual spectra of each of the plurality of lipids. To reconstruct the individual spectra, the deconvolution of said list of LC-MS-based mass features may comprise the step of clustering the LC-MS-based mass features based on locations and intensity profiles along a retention time (RT) dimension in order. Hence, said LC-MS-based mass features may be pooled or grouped in accordance to their locations and intensity profiles along the retention time (RT) dimension so as to reconstruct the individual spectra.

Without being bound by theory, the clustering or pooling step above may involve the use of an algorithm known in the art, such as quality-threshold clustering or other suitable grouping algorithms. An average correlation coefficient in the range from about 0.65 to about 0.75, such as about 0.65, about 0.66, about 0.67, about 0.68, about 0.69, about 0.70, about 0.71, about 0.72, about 0.73, about 0.74 or about 0.75, may be required between pairwise features in each deconvoluted spectrum. Said correlation coefficient may refer to Pearson's correlation coefficient.

In an embodiment, to ensure correct spectral reconstruction, a second routine may set forth low variation in intensity ratio for pairwise mass features, among all samples. The requirement of constancy in ratio may be valid even if concentrations vary among samples, as long as analytical conditions remain largely unchanged. In a descending manner, starting from the LC-MS-based mass feature with the highest signal-to-noise ratio, if such LC-MS-based mass feature increases the overall coefficient of variation to 15%, 16%, 17%, 18%, 19%, 20%, 21%, 22%, 23%, 24%, 25%, 26%, 27%, 28%, 29%, 30% or any values between 15% to 30%, it may be removed from the spectrum. The removed features may be collectively treated as newly-generated spectrum, and the procedure may be repeated on it in a cascading manner. At its conclusion, the resulting spectra may be allowed to overlap in member features, in order to accommodate highly similar lipids.

The inference of the daughter ions in the method as defined herein may comprise the step of matching mass-to-charge (m/z) values of the reconstructed individual spectra with a database to obtain a list of candidate exact-masses from which the one or more parental exact masses will be extracted. The database used may comprise an in-source fragment database, a specific adduct database or a combination thereof. Hence, the step of matching mass-to-charge (m/z) values of the reconstructed individual spectra with the database above may involve the use of a combination of one or more databases.

The m/z matching threshold is maximally two-times machine resolution in ppm. For the sake of clarity and for the purpose of illustrating the m/z matching threshold, if the machine has a resolution of 5 ppm, the m/z matching threshold should therefore be less than 10 ppm. If the resolution of the machine is 10 ppm, the m/z matching threshold should therefore be less than 20 ppm.

The step of inferring the daughter ions in the method above may further comprise a presumptive screening step, in which it may comprise the step of iteratively assigning individual m/z values in each spectrum with a list of product ions to account for the inferred daughter ions absent in the database(s). The resulting candidate exact-mass M may be determined by equation (i) provided below, given electric charge of the product ion (Z), the change in parental mass due to the ionization ($\Delta M_A$), and the number of parents making up the ion (N):

$$(Z \times m/z - \Delta M_A)/N \qquad (i)$$

The identification of the one or more parental exact masses in the method described here further comprises the step of grouping all candidate exact masses in the list of candidate exact-masses into one or more groups of candidate exact-masses, each candidate exact-mass within a group having an exact-mass within an average spacing of less than two-times machine resolution with neighboring candidate exact-mass in the group. For the sake of clarity, for the machine that has a resolution of 5 ppm, the average spacing should be less than 10 ppm. If the resolution of the machine is 10 ppm, the average spacing should therefore be less than 20 ppm.

The method as defined herein may further comprise scoring each of the one or more parental exact masses based on the inferred daughter ions, in which it may comprise calculating a feature score based on the database m/z matching step and the presumptive screening step as described in the following section.

Feature Score Based on Database m/z Matching

The incremental score contributed by a spectral match ($N_M$) is inversely proportional to the database number of exact masses ($S_{m/z}$) with the same m/z value and may be calculated by formula (ii) below.

$$S_{m/z} = 6/(N_M + 1) \qquad (II)$$

The ability of the score to discern predictions may depend on the availability of the database.

Feature Score Based on Presumptive Inference

Here, a confidence score may be assigned according to prior knowledge of the inferred product ion: features annotated with common product-ions may be given 3 points, while 2 points may be assigned to those that are otherwise also observed in mass spectra. For explorative analysis, ion species may be assigned a score of one point. The score based on m/z matching may be used if there is also one based on presumptive inference.

The calculation of the feature score above has the advantages to eliminate the drawbacks of determining the feature score based on the individual method: database m/z matching and presumptive screening as outlined in Table 1 below.

TABLE 1

Comparison of methods for daughter ions screening.

|  | Presumptive daughter screening | Database m/z screening |
|---|---|---|
| Relevant daughter type | Either common, or for explorative purpose | High specificity to small number of defined lipid classes |
| Processing speed | Faster | Slower |
| Knowledge discovery | Allow exploration to cover knowledge gap | Restricted to prior knowledge |
| Relative reliability | Lower | Higher |

The method of identifying the plurality of lipids in the sample profiled using the combined LC-MS technique as defined above may comprise the step of determining each of the plurality of lipids based on characteristic mass features, which comprises the step of matching unique masses with an organism-specific mass database. Said database may be suitably selected from available ones, such as the Kyoto Encyclopaedia of Genes and Genome (www.genome.jp/kegg), the Human Metabolome Database (www.hmdb.ca), LIPID MAPS (http://www.lipidmaps.org/) or the LipidBlast (http://fiehnlab.ucdavis.edu/projects/LipidBlast).

After shortlisting candidate species (i.e. the candidate exact-masses), the parental lipid may be identified as the one with the most m/z matches, by matching the set of values constituting the deconvoluted spectra, against a database having a plurality of characteristic m/z values, of lipids having the same exact-mass. There is a match if the difference in m/z values is within two-times machine resolution in ppm. For the sake of clarity, for the machine that has a resolution of 5 ppm, a m/z value may be deemed to match with a said database value if their difference in values is less than 10 ppm. If the resolution of the machine is 10 ppm, the m/z value may be deemed to match with said database value if the difference in m/z values is less than 20 ppm.

As aforementioned, the method as defined herein may comprise the step of validating a lipid of the plurality of lipids, in which such a step comprises confirming that an ion annotation of a most intense mass feature corresponds to one of a preferred product-ion for a lipid class to which the lipid belongs, as described in Table 2 below showing the list of dominant daughter ions for individual lipid classes.

TABLE 2

List of dominant daughter ions for individual lipid classes.

| Daughter-ions | Acquisition mode | Specificity |
|---|---|---|
| $[M + H]^+$ | Positive | Common, but not DG, TG, Cer |
| $[M + Na]^+$ | Positive | Common, but not PE, pPE, LysoPE |
| $[M - H]^-$ | Negative | Common |
| $[M + CH_3COO]^-$ | Negative | Common |
| $[M + NH_4]^+$ | Positive | DG, TG |
| $[M + H]—C_2H_8NO_4P$ (−141) | Positive | PE, pPE, LysoPE |
| $[M + H/Na]—C_3H_8NO_6P$ (−185) | Positive | PS |
| $[RCOO + 58]^+$ | Positive | FA |

TABLE 2-continued

List of dominant daughter ions for individual lipid classes.

| Daughter-ions | Acquisition mode | Specificity |
|---|---|---|
| $[M + H—H_2O]^+$ | Positive | Sphingolipid, MG, DG |

Abbreviations:
Diglyceride (DG);
Fatty acid (FA);
Monoglyceride (MG);
Phosphatidylserine (PS);
phosphatidylethanolamine (PE);
Sphingomyelin (SM);
Triglyceride (TG);
pPE (plasmenylphosphatidylethanolamine)

The method as defined herein may further comprise the step of validating each of the plurality of lipids, in which such a step comprises selecting a lipid with a best parental exact mass score. In an embodiment, the validation of parental identity, in the method described herein, may further comprise the step of selecting the parent with the best exact-mass score, among those with the same most-intense feature. The parent is then reported with their confidence score, retention time and daughter intensities in all samples.

Once the parent species is identified, a validation step may be necessary. The step of validating each of the plurality of lipids may comprise identifying each lipid separately using a suitable method such as a tandem mass spectroscopy ($MS^2$) technique or raw spectral comparison with standards and/or in-house expert knowledge. A rigorous spectral validation may require minimally four matching known features, comprising the one with the highest intensity (lead), and three others with consistent relative intensities. When RT knowledge is available for verification, similar requirement for matching the lead and two other features may have to be fulfilled.

The ionization mode relevant in the method described herein may be electrospray ionization (ESI).

As previously discussed, the method described herein may be used to identify the plurality of lipids in any organism, provided there is sufficient extract and an organism-specific database.

The method described herein may be used to identify lipids undergoing in-source fragmentation. The salt assortments and concentrations in the LC mobile phase may be also tweaked to generate at least four distinctive mass features for each lipid class.

The method described herein may not require a user to have a deep expertise in metabolomics and/or lipidomics to perform the identification, based on software implementing said method. Therefore, advantageously, the method described herein may be performed in an automated and high-throughput manner.

In a further embodiment, the method as described above may involve the step of inferring one or more daughter ions, wherein the one or more daughter ions may be dominant daughter ions.

In an embodiment, the term "framework" and "method", in particular in relation to the use of the term "method" in "method of identifying a plurality of lipids in a sample that is profiled using a combined Liquid Chromatography-Mass Spectrometry (LC-MS) technique as defined herein" may be used interchangeably, unless specified otherwise.

Therefore, the disclosure also provides a framework of identifying a plurality of lipids in a sample in accordance with the present embodiments that is profiled using a combined Liquid Chromatography-Mass Spectrometry (LC-MS) technique, comprising the steps of:

a) providing a list of Liquid Chromatography-Mass Spectrometry (LC-MS)-based mass features;

b) deconvoluting said list of LC-MS-based mass features;

c) inferring daughter ions from the deconvoluted list of LC-MS-based mass features;

d) identifying one or more parental exact masses from the inferred daughter ions;

e) scoring each of the one more parental exact masses based on the inferred daughter ions;

f) determining characteristic mass features in response to the scoring of each of the one or more parental exact masses; and g) determining each of the plurality of lipids based on the characteristic mass features thereof.

Further, the framework as defined above may further comprise the step of validating the inferred daughter ions and/or the plurality of lipids. Therefore, the framework of identifying a plurality of lipids in a sample that is profiled using a combined Liquid Chromatography-Mass Spectrometry (LC-MS) technique above may comprise the steps of:

a) providing a list of Liquid Chromatography-Mass Spectrometry (LC-MS)-based mass features;

b) deconvoluting said list of LC-MS-based mass features;

c) inferring daughter ions from the deconvoluted list of LC-MS-based mass features and optionally validating the inferred daughter ions;

d) identifying one or more parental exact masses from the inferred daughter ions;

e) scoring each of the one more parental exact masses based on the inferred daughter ions;

f) determining characteristic mass features in response to the scoring of each of the one or more parental exact masses; and g) determining each of the plurality of lipids based on the characteristic mass features thereof and optionally validating each of the plurality of lipids.

Accordingly, the advantages and/or benefits of the method as described in the present disclosure may also be applicable to the above framework.

Exemplary, non-limiting embodiments of use of the method of identifying a plurality of lipids in a sample that is profiled using a combined Liquid Chromatography-Mass Spectrometry (LC-MS) technique as defined herein, will now be disclosed.

As outlined above, the present disclosure also provides the use of the method as defined above to identify a plurality of lipids undergoing in-source fragmentation.

Similar as above, the present disclosure also provides the use of the framework as defined above to identify a plurality of lipids undergoing in-source fragmentation.

Thus, it can be seen that the present embodiment provides the method of identifying the plurality of lipids that is capable of improving the accuracy in the lipid analysis. Such method may be useful when implemented in one of the circumstances below or combinations thereof:

a) when the prospect of rigorous validation is limited or not immediately available. For example, researchers may need to rapidly generate biological hypotheses, while awaiting time-consuming verification;

b) when dealing with a large number of datasets where it may be impractical to conduct exhaustive confirmatory analyses; and c) when new samples are rare, difficult to obtain, replicate or maintain. Under such situations, as long as feature density is reasonably high, the combination of the method described herein with validation using raw spectral inspection, may be sufficient to construe reasonable hypotheses.

It can be thus concluded that the method described herein may represent a significant development for the first MS stage that may be used integrally with other advancements in mass-spectrometry and liquid-chromatography-based techniques.

While exemplary embodiments have been presented in the foregoing detailed description of the invention, it should be appreciated that a vast number of variations exist. It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of steps and method of operation described in the exemplary embodiment without departing from the scope of the invention as set forth in the appended claims.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 is a chart illustrating the framework for LC-MS-based lipidomics as described in the present invention. As outlined in the detailed description, the framework (i.e. the method of identifying the plurality of lipids in a sample comprises spectral deconvolution (step 1), hybrid daughter-ions screening (step 2), parents identification (step 3), and parents validation (step 4). Only two sources of prior-knowledge were used for identification: the LipidBlast library for m/z screening in step 2, and the compiled list of preferred product ions used in step 4 (Table 2). Any other cited species of validated parents were screened presumably from an arbitrary list of daughter ions in step 2.

FIG. 2 is a number of schemes and graph to describe the collision-induced dissociation in $MS^2$ experiments; FIG. 2a illustrates the characteristic fragmentation locations, which are marked by arrows for glycerolipids, glycerophospholipids and sphingolipids; FIG. 2b depicts that the resulting m/z signatures for fingerprinting lipids are stored in knowledge-base; an example for PC 18:1/18:4 (Lecithin) is depicted.

FIG. 3 is a number of charts to assess the effectiveness of the method (i.e. framework). This fig. describes, in particular, overall coverage in four major lipid families, based on separate identifications from both positive and negative acquisition modes. For GPL, there is one identified phosphatidylglycerol (PG), lyso-PC and semilysobisphosphatidic acid species. Left bottom panels: no. species identified in each acquisition mode at predefined confidence level; corresponding numbers with sufficient intensity for verification either by $MS^2$ technique or spectral signature; final confirmed no. lipids. Four species (fatty alcohols and cholesterols) are not within scope of the experiment.

FIG. 4 is a number of mass spectra obtained from the $MS^2$ validation profiles of the sample in the a. positive and b. negative acquisition modes.

FIG. 5 is a number of charts describing number and proportion of true positive predictions at score thresholds of 6 (two cartoon peaks), 9 (three cartoon peaks) and 12 (4 cartoon peaks).

FIG. 6 is a number of charts describing the uncovered lipid profiles based on an independent exploratory study of the same Chinese hamster ovary (CHO) dataset.

FIG. 7 is a number of histograms describing the number of required features for identification, among lipids of sufficiently high intensity.

FIG. 8 is a number of combined histograms for both modes (i.e. positive and negative modes) at 100% true positive rates (score 12.0).

FIG. 9 is a chart describing the profiles of detected daughter ions; In particular, it describes the relative numbers of non-specific and characteristic daughter instances in the positive mode.

FIG. 10 is a number of charts describing the profiles of detected daughter ions; In particular, they describe fraction of individual lipid classes with the most prevalent characteristic daughter (positive mode).

FIG. 11 is a number of charts describing the profiles of detected daughter ions; In particular, they describe the proportion of lipid classes having top six detected daughter ions. SM: Sphingomyelins; CL: Cardiolipins; PS: Phosphatidylserines; PC: phosphatidylcholines; PI: Phosphatidylinositols; PE: phosphatidylethanolamines; pPE: Plasmenylphosphatidylethanolamine; GLS: Gangliosides; Cer*: Ceramide and glycosphingolipids; TG: Triglycerides; DG: Diglycerides; FA: Fatty acids; PG: phosphatidylglycerol.

FIG. 12 is a chart describing the p-values (probability values or asymptotic significances) of product-ions representation in various lipid classes, according to Fisher's exact test.

FIG. 13 is a number of charts describing the relation between lead-feature profile and validity of identification. In particular, they describe verification profiles for features annotated with correct or incorrect preferred product ions (score >9.0).

FIG. 14 is a number of histograms describing the relation between lead-feature profile and validity of identification. In particular, it depicts the erroneous preferred product ion for negative controls.

FIG. 15 is a number of charts describing the proportion of lipid classes with preferred product ions that are also characteristic. The pie chart depicts the distribution of preferred product ions; unlabeled species are [RCOO+58]$^+$ and [M+H]—$C_3H_8NO_6P$ (−185), respectively.

EXAMPLES

Non-limiting examples of the invention and a comparative example will be further described in greater detail by reference to specific Examples, which should not be construed as in any way limiting the scope of the invention.

Sample Collection and Preparation

Sample Collection

Suspension-adapted Chinese hamster ovary (CHO) K1 cells were grown in protein-free media comprising of 50% HyQ PF-CHO (purchased from HyClone Laboratories Inc. of South Logan, Utah of the United States of America) and 50% CD CHO (purchased from Gibco-Invitrogen of the United States of America), supplemented with 1 g/L sodium bicarbonate, 6 mM L-glutamine and 0.05% Pluronic F-68 (purchased from Invitrogen of Carlsbad, Calif. of the United States of America). The stable recombinant SH-87 cell line expressing anti-HER2 monoclonal antibody was generated from CHO K1 and cultured in protein-free media comprising of 50% HyQ PF-CHO and 50% CD CHO, supplemented with 1 g/L sodium bicarbonate, 8 mM L-glutamine, 0.05% Pluronic F-68 and 600 µg/mL geneticin (G418, purchased from Sigma-Aldrich of Saint Louis, Mo. of the United States of America). All cell lines were maintained at 37° C. in 8% $CO_2$ in single-use Erlenmeyer flasks (purchased from Corning Life Sciences of Acton, Mass. of the United States of America), sub-cultured every 3-4 days. Cells were harvested at exponential growth phase.

Sample Extraction $1 \times 10^7$ cells were obtained at the mid-exponential phase (day 4) of replicate CHO-K1 and SH-87 cultures. The cells were quenched in 5 volumes of ice-cold 150 mM sodium chloride (purchased from Sigma-Aldrich of Saint Louis, Mo. of the United States of America) solution and centrifuged for 3 minutes at 1250 g and 4° C. The resulting solution was aspirated and 400 µL of ice-cold methanol (optima grade, purchased from Fisher Scientific of Hampton, N.H. of the United States of America) was added to the cell pellet.

The re-suspended cells-methanol mixture was transferred to a 2-mL sample tube containing 200 µL of chloroform (purchased from Merck of Kenilworth, N.J. of the United States of America). Subsequently, 900 µL of cold methanol and 3.8 mM tricine (purchased from Sigma-Aldrich of Saint Louis, Mo. of the United States of America) (9:10) mixture, followed by the addition of 500 µL of chloroform to the sample tube. The mixture was then vortexed for 30 to 60 seconds after the addition of each solution. The sample was then centrifuged at 18,000 g for 20 minutes at 4° C.

800 µL aqueous methanol-tricine layer was transferred to a clean tube. A further 700 µL of cold methanol and 3.8 mM tricine (9:10) mixture was added to the chloroform phase, which was then centrifuged at 18,000 g for another 10 minutes at 4° C. 1 mL of the aqueous layer was extracted and combined with the first aqueous extract, while the chloroform layer was transferred to a clean glass vial. Both extracts were stored at −80° C. The non-polar chloroform extracts were dried and concentrated 2 times in an isopropanol-acetonitrile-methanol-water (5:2:2:1) mixture (all solvents were obtained from Fisher Scientific of Hampton, N.H. of the United States of America, optima grade) containing 0.1% acetic acid (purchased from Merck of Kenilworth, N.J. of the United States of America) and 0.1% ammonia solution (obtained from BDH Chemicals of Dawson, Ga. of the United States of America).

Liquid Chromatography (LC)

Sample was separated using ultra performance liquid chromatography (Acquity; obtained from Waters of Milford, Mass. of the United States of America), with a reverse phase column (Kinetex C18 100 Å, 1.7 µm, 2.1 mm×50 mm; purchased from Phenomenex of Torrance, Calif. of the United States of America). The mobile phase consisted of solvents 'A' and 'B'; 'A' is a 2:2:1 mixture of acetonitrile (Gradient grade; purchased from Merck of Kenilworth, N.J. of the United States of America), methanol (Optima grade; obtained from Fisher Scientific of Hampton, N.H. of the United States of America) and water, with 0.1% acetic acid (ACS, ISO, Reag. Ph Eur; obtained from Merck of Kenilworth, N.J. of the United States of America) and 0.1% ammonia (25% AnalaR NORMAPUR; purchased from VWR International of Radnor, Pa. of the United States of America) solution; 'B' is isopropanol with 0.1% acetic acid and 0.1% ammonia solution. The column was first equilibrated for 0.5 minutes at 1% B. The gradient was then increased from 1% B to 90% B over 9.5 minutes before a 0.3 minutes wash at 90% B and 1.7 minutes re-equilibration step to 1% B. The flow rate was set to 500 μL/minute at 30° C.

Mass Spectrometry (MS)

The eluent was then directed into the mass spectrometer (Xevo G2 electrospray ionization [ESI]-quadrupole time-of-flight [Q-TOF] purchased from Waters of Milford, Mass. of the United States of America) operating in full scan mode. Capillary and source voltages were 3 kV and 40 V, and, 2 kV and 40 V, for positive and negative modes, respectively. Source and dissolution gas temperatures were set at respective 120° C. and 600° C. The continuous flow of leucine-enkephalin was used as internal lock mass. The MS analyzer was set to 'sensitivity' mode, with a resolution >10,000 full width at full-width-at-half-maximum (FWHM), and accuracy <10 ppm root mean square (RMS) error.

Mass Feature Extraction

Mass features were extracted from raw data using the following 'centWave' algorithm parameters: snthresh=1.5, ppm=15, prefilter=c(0,0) and peakwidth=c(5,20). Subsequently, the same features in different samples were identified using a m/z-matching algorithm and then aligned according to their RT-value. In total, two runs of consecutive m/z matching and RT alignment were carried out. Isotopes were accounted for as previously described.

Optimization of Pre-Processing Parameters

Fifteen parameters of the pipeline shown in Table 3 were optimized, using a previously-described Genetic Algorithm to maximize identifications with confidence score ≥9.0. Briefly, 64 initial sets of parameter values were randomly chosen with replacement within stipulated ranges to run independent pre-processings, and each was scored by the number of lipid identifications (confidence score >9). The top-performing 50% (32) of parameter-sets were retained ('fitness selection') and duplicated, after which, each linear parameter-set was subjected to a 'chromosomal crossover' with another, at a random juncture with 50% probability. Parameter values may be swapped as such. Following on, for each set, two parameters were randomly chosen and their value replaced by sampling their stipulated range ('gene mutation'). The new generation of parameter-sets were again used to conduct pre-processing for scoring purpose, then went through the same round of 'selection', 'duplication', 'crossover' and 'mutation', to generate the next generation, and so on. The repetitive procedure was stopped when the generational best score stabilized for at least 50 generations.

TABLE 3

Genetic algorithm-optimized pipeline parameters for CHO cell lines case study.

| GA parameters | Optimized value (Positive mode) | Optimized value (Negative mode) | range [start, end, increment] | Unit |
| --- | --- | --- | --- | --- |
| m_pgmzerra[1] | 55 | 30 | [30, 60, 5] | ppm |
| m_slicewida[2] | 6 | 7 | [6, 18, 1] | sec |
| m_pgmzwin[3] | 1.1 | 0.3 | [0.1, 2, 0.1] | m/z |
| m_clustwtrt[4] | 1 | 1.4 | [0.2, 0.2, 2] | sec |
| m_clustwtmz[5] | 0.4 | 0.4 | [0.2, 0.2, 2] | m/z |
| m_FPGmzppm[6] | 25 | 25 | [5, 25, 1] | ppm |
| m_gpgmzppm[7] | 25 | 9 | [5, 25, 1] | ppm |
| m_rtcorrpts[8] | 0.05 | 0.5 | [0.05, 0.5, 0.025] | — |
| m_xmlscaninterval[9] | 0.22 | 0.2 | [0.18, 0.22, 0.02] | |
| m_xmlmzbuffer[10] | 0.02 | 0.01 | [0.01, 0.02, 0.01] | m/z |
| m_ipcrtrange[11] | 22 | 23 | [2, 25, 1] | sec |
| m_ipcminoverlap[12] | 0.2 | 0.15 | [0.05, 0.5, 0.05] | — |
| m_ipcminmergeoverlap[13] | 1 | 1 | [0.5, 1, 0.05] | — |
| m_predmzerr[14] | 20 | 22 | [20, 40, 1] | ppm |

[1]Minimum m/z separation between features
[2]Sliding RT-window size used in matching same feature across samples (peak-grouping)
[3]Sliding M/Z-window size used in matching same feature across samples (peak-grouping)
[4]RT weightage in separating unresolved peak-groups by K-means clustering
[5]m/z weightage in separating unresolved peak-groups by K-means clustering
[6]Maximum allowable m/z error within a peak-group
[7]Maximum allowable m/z error of 'good' peak-groups used for RT correction of global peak-groups
[8]Data span in term of proportion for RT correction
[9]Involved in determining the intensity profile of features in the RT dimension
[10]Involved in determining the intensity profile of features in the RT dimension
[11]Involved in determining the intensity profile of features in the RT dimension
[12]Parameter for combining similar spectra
[13]Parameter for combining similar spectra
[14]Affects feature participation in determination of exact masses Lipid Databases for Identification Lipid candidates were partially confirmed based on masses in various publicly available databases such as: the Kyoto Encyclopaedia of Genes and Genome (www.genome.jp/kegg), the Human Metabolome Database (www.hmdb.ca), LIPID MAPS (http://www.lipidmaps.org/) and the LipidBlast (http://fiehnlab.ucdavis.edu/projects/LipidBlast). Class identities were based on characteristic features in lipidBlast and an accessible database (which for these non-limiting examples was an available in-house database).

Pre-Processing Framework

Step 1: Spectra Deconvolution

Step 1.1 LOESS-Based Intensity Correction

The intensity drift for each mass feature was corrected across the batch-run to support subsequent intensity-based analyses. Following a known procedure, a non-parametric regression of the intensities in quality control (QC) samples according to run order was carried out using 'LOcal regrESSion' (LOESS) technique. A linear or quadratic function was auto-fit by minimizing tri-cubic-weighted least-square error parametrically, while the optimal data span was determined by using the prescribed leave-one-out cross-validation approach. Based on the resulting model, a cubic-spline curve was then interpolated for all samples. For the sake of clarity, all samples here were corrected including the QC samples. Subsequently, the intensities of the mass feature were corrected in all samples to negate the drift modelled by the spline curve.

Step 1.2 Quality-Threshold Features Clustering

To deconvolute the spectra of individual lipid species, a quality-threshold clustering algorithm, which has been previously used for feature alignment was repurposed. The spectra of suspect molecules were reconstructed by clustering features with similar locations and intensity profiles along the RT dimension, thus effectively identifying daughter product-ions with comparable elution profiles. In evaluating the similarity, on average, a Pearson's correlation coefficient of 0.7 between pairwise features in a spectrum was required.

Step 1.3 Spectral Analysis of Intensity Ratio

In order that each spectrum is correctly reconstructed, a second routine ensured low variation in intensity ratio for pairwise mass features, among all samples. This requirement of constancy in ratio is valid even if concentrations vary among samples, as long as analytical conditions remain largely unchanged. In a descending manner, starting from the feature with the highest signal-to-noise ratio, if a feature increased the overall coefficient of variation above 15%, it was removed from the spectrum. The removed features were collectively treated as newly-generated spectrum, and the procedure was repeated on it in a cascading manner. At its conclusion, the spectra were allowed to overlap in member features, in order to accommodate highly similar lipids.

Step 2: Hybrid Daughter-Ions Screening

Step 2.1 Database m/z Screening

For each feature of every deconvoluted spectrum, m/z values were matched with those in a spectral database (±10 ppm) to obtain the corresponding list of parental exact-masses.

Step 2.2 Presumptive Screening

Independent of the spectral screening, each mass feature in every spectrum was also iteratively assigned with product-ions from a candidate list to account for potential daughters absent in the spectral database. Given the electric charge of a product ion (Z), the change in parental mass due to the ionization ($\Delta M_A$), and the number of parents making up the ion (N), the inferred exact mass M is given by: $(Z \times m/z - \Delta M_A)/N$.

As an example from the pPE 34:1 spectrum, if a feature with m/z value=1,426.065 was assigned the $[2M+Na]^+$ ion, then the electronic charge Z can be understood to be +1 from the formulae while the change in product mass due to the inclusion of a sodium ion is $M_A$=+22.989. As there were two parent molecules in the daughter ion (N=2), it can be inferred the parental mass as: $(1 \times 1,426.065-22.989)/2$=701.538 g/mol.

Step 2.3 Exact Masses Deduction

Sorted parental mass values with less than 10 ppm average spacing were considered redundant and therefore they were grouped together and their values averaged.

Step 2.4 Scoring of Exact Mass

The confidence score of each parental mass was summed from contributing feature scores, calculated as follow:

Feature score based on database m/z screening

The incremental score contributed by a spectral match is inversely proportional to the database number of exact masses with the same m/z value:

$S_{m/z}=6/(N_M+1)$.

A conservative fudge value of 1 was added to the denominator while a numerator constant of 6 was introduced to scale the upper-bound score to 3. The reliability of the scoring depends on the availability of a comprehensive organism-specific database.

Feature score based on presumptive screening of product ions

Here, a confidence score was assigned according to prior belief of the prevalence of a product ion underlying the spectral data (ESM Table 3): features annotated with common product-ions, such as those in Table 2, were given 3 points, while 2 points were assigned to the rest that were somewhat observed in mass spectra. For explorative analysis, ion species were assigned a score=1. The score based on m/z screening was used if there is also one based on presumptive inference.

Step 3: Parents/Species Identification

Unique masses were then database-matched (±10 ppm) to identify organism-specific lipids with the largest number of characteristic m/z matches (±10 ppm).

Step 4: Parents Validation

Step 4.1 Preferred Product Ions Analysis

For each identified parent, the ion annotation of its most intense peak was verified, to correspond to one of preferred product-ions for its lipid class, according to Table 2. Inconsistent predictions were then filtered away.

Step 4.2 Selection of Parents with Best Scores

Among valid parents sharing the same feature with the highest intensity, those with the highest confidence score were selected, and then reported with their score and daughter profiles (product ion annotation, m/z, RT, intensity) in all samples.

Framework Implementation

Framework was implemented in Java, and called the LOESS package in the R software environment for intensity correction. Both the pipeline, and the Genetic Algorithm used to optimize its parameters, were deployed on a 64-bit Windows Server (2012 R2 Datacenter) with four 8-core CPU (Intel_Xeon_E5-4650 0 @2.7 GHz) and 768 GB of installed memory.

The term "framework" referred to in this section may be used interchangeably with the term "method" in the phrase "method of identifying plurality of lipids in a sample that is profiled using a combined Liquid Chromatography-Mass Spectrometry (LC-MS) technique".

Statistical Association of Lipid Classes with Product Ions

For each lipid class, the presence (or absence) of a product ion was evaluated for statistical significance using Fisher's exact test for two categorical variables at two levels. A 5% p-value cut-off was used with resultant q-values well below 10%.

Systematic LC-MS-Based Lipidomics Pre-Processing Framework

FIG. 1 illustrates the procedure of the framework (i.e. the method of identifying the plurality of lipids) described above. After extracting mass features from the raw data, and matching them across samples (refer to sample collection and preparation), the features were clustered into spectra, representing individual underlying lipids based on similar locations and shapes in the RT dimension (step one). Then, a two-phase plan to uncover their identity was implemented. The strategy was to adequately consider both the peculiarity of a diverse range of daughters to molecular subsets, and the preferred product ions for each metabolite class. Without such deliberations, a simplistic approach of expanding the list of daughter species under consideration, will instead, overwhelmingly increase the number of false parent candidates.

A hybrid approach to infer appropriately both common and specific daughters (step two) was used, so as to improve accuracy, and coverage of parent deduction (step three). Then, the basic knowledge on the preferred product ions was used, for each lipid class, to distinguish true parents from false ones, together with their corresponding sets of daughter-ions (step four).

In the first phase of the framework, the hybrid approach in step two was designed to robustly enhance inference of product-ions with differing relevance among lipid classes (refer to Table 3). Specifically for common daughters, their presences in every spectrum were presumed accordingly, and hence their possibilities were evaluated for all constituent features. The eventual accuracy was expected to be acceptable with the additional advantages of rapid processing and broader coverage.

The method further allows for screening of poorly-characterized daughter-ions to reduce knowledge gap, by assigning them low score to maintain overall reliability of identification. Otherwise, the accuracy in product-ions and precursors prediction was unacceptably high with presumptive screening. Then, database m/z screening will be more appropriate with lower error rate, for daughters that are specific to a small number of parent classes. However, the drawbacks can be slower processing and limited database knowledge.

While any library or combination of libraries can be used in accordance with the present embodiments, to ensure diverse and expansive coverage in these non-limiting examples, the publicly available LipidBlast database (119341 parent species in 29 classes) was used in addition to an available in-house library for m/z screening. The resource on collision-induced dissociations (FIG. 2a) was believed to be reliable for 'fingerprinting' those parent species (FIG. 2b) undergoing in-source fragmentation; other empirical databases can be used, as when available. Indeed, both common and specific product-ions contributed to forming a confident profile of suspect molecules. For this purpose, the information was pooled together in the form of a parent confidence score (step two in FIG. 1) for which, a higher value would reflect recovery of (1) common daughters that should be present, and (2) those which are highly specific to the parent lipid.

After parent identification (step 3), in the second phase of pre-processing (step 4), the elementary information on the preferred modes of ionization was used to discriminate alternative parent hypotheses for the same spectra. To elaborate, certain common product-ions such as [M+Na]$^+$ and [M−H]$^-$, were dominantly formed across lipid classes under standard analytical conditions, and as such, one of them typically accounts for the most intense (leading) feature in each spectrum. There were also dominant daughter species that are either only relevant to some lipid classes ([M+H−H$_2$O]$^+$) or highly specific to a class ([M], [RCOO+58]$^+$, [M+NH$_4$]$^+$).

As ESI is considered 'soft', parent fragmentation is generally not predominant, and happens with low (but detectable) probabilities. For this reason, it is generally not used for fingerprinting lipids, and only one dominant species was observed, each for PE ([M+H]−141), and PS ([M+H/Na]−185). With the assumptions of preferred product ions for each lipid class compiled in Table 4, parents identified in step 3 were verified based on the inferred identity of its leading feature. Thus, the second phase further improved identification accuracy in a feedback manner. Moreover, the required presence of dominant daughter ensured availability of the most intense feature for subsequent comparative analysis. In this regard, dominant daughters were generally not associated with distinctive ones, allowing one to use both information for identification. The technical details of the framework are as defined above.

TABLE 4

Preferred product ions of individual lipid classes.

| Product ions | Mode | Specificity | Comments |
| --- | --- | --- | --- |
| [M + H]+ | + | Common | Assumed |
| [M + Na]+ | + | Common | Assumed |
| [M − H]− | − | Common | Assumed |
| [M + CH$_3$COO]− | − | Common | Assumed |
| [M + NH$_4$]+ | + | DG$^b$, TG$^c$ | In-house data |
| [M + H]-141$^a$ | + | PE$^d$, pPE$^e$, Lyso-PE | In-house data |
| [M + H/Na]-185$^a$ | + | PS$^f$ | In-house data |
| [RCOO + 58]+ | + | FA$^g$ | In-house data |
| [M + H—H$_2$O]+ | + | SPL$^h$, MG$^i$, DG$^b$ | In-house data |

$^a$Masses of 141 and 185 refer to respective C2H$_8$NO$_4$P and C$_3$H$_8$NO$_6$P head-group moieties;
$^b$Diglycerides;
$^c$Triglycerides;
$^d$phosphatidylethanolamines;
$^e$Plasmenyl-phosphatidylethanolamine;
$^f$Phosphatidylserines;
$^g$Fatty acids;
$^h$Sphingolipids;
$^i$Monoglyceride Framework Offers Sufficient Coverage for Rapid Generation of Biological Hypotheses The framework to profile two CHO cell lines was applied, so as to compare the differences between recombinant producers and non-producers. Besides spectral knowledge-base search for product-ions, some daughter species, such as [M+NH$_4$]$^+$ and [M+H]−H$_2$O, were also screened presumptively in order to cover current knowledge gap on their prevalence. Additionally, some less prominent but relevant ions, e.g. [M+H−C$_6$H$_{10}$O$_5$]$^+$ species, were surveyed with low score to mitigate the risk of false prediction.

Based on confidence threshold equivalent to two features, a total of 114 and 54 top-ranking species were flagged in the respective positive and negative acquisition modes (left bottom panel of FIG. 3). Of these, 20 and 4 corresponding lipids could not be subjected to MS$^2$ validation due to their low observed intensities («1 E4 a.u.). They were then inspected based on the in-house knowledge of their chromatographic and mass-spectroscopic profiles, resulting in 10 confirmed lipids. Of the 94 and 50 separate predictions with sufficient intensities, an aggregate of 91 species were accordingly affirmed either using MS$^2$ technique or spectral inspection (shown in FIGS. 5a and 5b). The final tally of 101 profiles come from 18 sub-classes of 4 major families (glycerophospholipids [GPL], glycerolipids [GL], SPL and FA), constituting one of the largest repertoire of the industrial workhorse (CHO cells) uncovered to date. Considering the usage of only LC/Q-ToF/MS data (average mass resolution), the number compared fairly well with the 250 species obtained from combined experimental methods.

From the profiles generated by the framework, at least two unmistakable molecular trends related to recombinant production can be observed, even before experimental validation. Firstly, the higher levels of longer-chain PC and PE species may allow supple membrane deformation in the producer cells (CHO-K1) for vesicular trafficking of recombinant proteins and lipid raft formation for the transport and functioning of required molecular machineries. The increased cellular expressions of longer-chain species were further evident in the CL and TG, which forms mitochondrial membrane and an important fatty acids reserve, respectively. Secondly, it was hypothesized that the producer cells have been able to develop enhanced resilience to cell cycle arrest and apoptosis by producing glycosylated/galactosylated derivatives of Cer and very-long-chain Cer. Both findings were also consistent with gene expressions of the associated enzymes based on microarray. Thus, it can be concluded that the framework as described here is able to generate valid hypotheses.

Framework is Accurate and Unbiased by User's Experience and Knowledge

Next, the accuracy profile of the framework (i.e. the method as described above) was evaluated. Firstly, among lipids with sufficient intensity to allow for $MS^2$ validation, the confirmation rates were positively correlated with confidence thresholds for both acquisition modes (FIG. 5), indicating that the scoring system appropriately weights relevant daughter ions. Secondly, the proportions were also largely comparable at high (both 100%), mid (89% vs. 92%) and low (82% vs. 72%) levels of confidence. Taking into account both modes, an 78% true positive rate was obtained, computed by [77+36]/[94+50] for the entire study. Thirdly, based on the same experimental dataset, (Table 5) the lipid repertoire was compared with those obtained independently from an XCMS-based method (using the same dataset), which presumes product-ions generically, and thus further requires ad-hoc knowledge of the user.

TABLE 5

Comparison of lipid identification approaches for CHO cell lines case study.

|  | Present approach | XCMS-based method |
|---|---|---|
| Coverage | 101 lipids | 57 |
| Diversity | 18 classes | 11 |
| Candidates | 168 | Thousands |
| Accuracy | 78% | <<10% |

Using the XCMS-based method, 57 lipids were identified in total based on a post-hoc evaluation of thousands of possibilities (refer to FIG. 6), indicating an accuracy of much lower than 10%. It can therefore be concluded that the method (i.e. the framework) described here appeared to require significantly less effort in combing through candidate lipids ([114+54] versus thousands), yet resulting in better coverage (101 versus 57) and diversity (18 versus 11).

It was further extrapolated, by inspection, a true positive rate of well over 90% in FIG. 5 if a similarly low coverage of 57 lipids was accepted. The number of features required for identification with the framework was also investigated. Remarkably, the median was just three for both modes, even without knowledge of the characteristic RT of the molecules (refer to FIG. 7), while four features were minimally required for attaining 100% true positives (FIG. 8). Thus, the usage of 4-5 spectral signature matching is recommended for validation, if the level of a species is too low for experimental confirmation.

Enhanced Daughter Inference Provides Basis for Accuracy and Coverage

The variety of identified daughters was classified in order to explore the basis of the improved inference over methods based on generic product ions. Ion profiles in the positive mode were used as an example due to its higher diversity, detectable in-source fragmentation and better coverage. As expected, only three common species, $[M+H]^+$, $[M+Na]^+$ and $[M+K]^+$, were needed to account for the bulk of detected instances (53% in FIG. 9), and thus, understandably, most conventional analyses focused on uncovering them in determining precursor lipids.

However, a sizable variety of ions remained unaccounted for, constituting almost half (47%) of detected instances with the method presented here. They consist of both adducts such as $[2M+H]^+$ and $[2M+Na]^+$ species, and fragments, with much lower prevalence compared to common product-ions. While some may be based on presumptive screening (step 2 of framework), their associated masses for certain classes of experimentally-verified lipids were observed with the systematic framework, such as the plausible $[M+H—C_6H_{10}O_5]^+$ species for hexose-derivatives of ceramides (Cer) (Table 6).

TABLE 6

Frequency of specific daughters detected in individual classes. They do not represent the exhaustive list of species used in parent identification.

| Class | Characteristic daughters | Count |
|---|---|---|
| Cer* (n = 5) | $[M + H]—H_2O$ | 5 |
|  | $[M + H—C_6H_{10}O5]+$ | 4 |
| CL (4) | $[M + NH_4]+$ | 4 |
| DG (2) | $[M + NH_4]$-sn3-18 | 2 |
|  | $[M + H]—H_2O$ | 2 |
|  | $[M + NH_4] +$ | 1 |
| FA (2) | $[RCOO + 58] +$ | 2 |
|  | $[RCO]+$ | 2 |
| GLS (2) | $[M + H]—H_2O$ | 2 |
| LysoPE (2) | $[M + H]—C_2H_8NO_4P$ (−141) | 2 |
|  | $[M+H]—H2O$ | 2 |
|  | $[M + H]—(C_2NH_5+ H_2O)$ (−61) | 2 |
| LysoPC (1) | $[M + Na]—C_3H_9N$ (−59) | 1 |
|  | $[M + H]—H_2O$ | 1 |
| PE (14) | $[M + H]—C_2H_8NO_4P$ (−141) | 12 |
|  | $[M + H]$-sn2 | 1 |
| pPE (7) | $[M + H]—C_2H_8NO_4P$ (−141) | 6 |
|  | $[M + H]—H_2O$ | 4 |
|  | sn1 ether + $C_2H_8NO_3P$ (+124) | 3 |
|  | $[M + Na]$-183-Na-sn2 | 2 |
|  | $[M + H]—C_2H_8NO_4P$-sn2 | 2 |
|  | $[M + Na]—C_2H_8NO_4P—Na + H$ | 1 |
|  | $[M + H]$-sn1 (alkenyl ether loss) | 1 |
| PS (5) | $[M + H]—C_3H_8NO_6P$ (−185) | 3 |
|  | $[M + H]$-sn2 | 1 |
| TG (20) | $[M + NH_4]+$ | 20 |
|  | $[M + NH_4]$-sn2-18 | 11 |
|  | $[M + NH_4]$sn1-18 | 9 |
|  | $[M + NH_4]$-sn3-18 | 7 |
| SM (6) | $[M + H]—H_2O$ | 1 |
|  | $C_5H_{15}NO_4P$ m/z = 184 | 1 |

Thus, with current knowledge gaps, depending on the experience of the user with their relevance, mass features can be examined irregularly for these ions in software, resulting in insubstantial identification.

The identification was also unreliable, since their precursor species could not be pre-confirmed, giving rise to a 'chicken and egg' situation for parent and daughter inference. However, with the hybrid approach, 8 uncommon adducts (FIG. 9) and a multitude of fragments (Table 6) were systematically determined, both from a presumptive list of more than a hundred product-ions, and a confirmed database of half a million characteristic features. Together, the daughters formed signatures for confirming parent classes on top of their exact masses. Particularly, the fragment proportion stands out in being more substantial compared to adducts (30% versus 17%), highlighting the importance of identifying them in LC-MS-based studies. To date, these are not considered routinely, as fragmentation by ESI is unintended, and poorly characterized.

Bearing in mind that the number of annotated features per parent species was critical for accurate identification (FIG. 5), this number increased considerably by 33%, from 2.14 instances per species considering just common daughters, to 2.84 with the inclusion of specific adducts, and to 3.34 instances per species after allowing for fragments (up 56%). Taking into account both specific adducts and fragments, the number improved 89% to 4.04 per species. In this light, the poor accuracy of conventional software may result from low feature counts based on common product-ions.

Signature Daughters are Critical for Inference

The prevalence of signature daughters from this study was reviewed. 79% of parent species in the positive mode have at least one specific daughter (pie chart in FIG. 10); 11 out of 14 lipid categories have more than 50% members with specific ions. Thus, a respectable portion of parent species may be 'fingerprinted' to some degree in LC-MS studies. To exemplify this point further, the top 6 most prevalent product-ions were profiled, including common ones, contributing to discovery in both acquisition modes.

The top ranking species in the positive mode, $[M+Na]^+$, which is already expected to be widespread, was present in 88% of all confirmed lipid spectra (FIG. 11). However, the lower proportions for $[M+H]^+$ (68%) and $[M+K]^+$ (56%) ions, were also considered to be 'common', suggesting the possibility that they may be discriminatory of parent classes, contrary to expectation. It was followed by 32% for $[M+NH4]^+$, 23% for [M+H]–141 and 22% for [M+H–]-1-120 species.

The prevalence of the above species in individual classes was interrogated, and the distinctive abilities of the lipids were found to generate even the most common daughters (FIG. 11). For example, with the possible exception of lysoPE, all seven detected classes of GPL were largely able to form the top three product-ions. On the other hand, the majority of SPL, as represented by Cer and glycosphingolipids (collectively Cer*), as well as gangliosides (GLS), markedly prefer $[M+H]-H_2O$ (100%) over $[M+K]^+$ (0%) species (Cer*: p-value for $[M+K]^+$<0.05; p-value for $[M+H]-H_2O$<0.001, FIG. 12). Similarly, the GL classes of DG and TG were likely to be without $[M+H]^+$ ions (under-presentation p-values <0.05 and 0.001 for respective 0% and 5% proportion). Instead, they had a higher propensity to form the highly characteristic $[M+NH_4]^+$ species (TG: p-value <0.001). Likewise, cardiolipins (CL) displayed a unique ability among GPL to produce the adduct (p-value <0.01). This information should be used for developing future lipidomics pipelines.

Distinctive daughters were also observed in the negative mode. While $[M+CH_3COO]^-$, $[M-H]^-$ and $[M+HCOO]^-$ were among the most widespread, they were detected in just 64%, 58% and 33% of all lipids in the same order. However, Cer* have all three adducts with 100% coverage (respective p-value <0.05, 0.01 and 0.001). On the other hand, the presence of $[M-CH_3]^-$ and the absence of $[M-H]^-$ species were hallmarks of phosphatidylcholines (PC) (p-value <0.05 and <0.001 respectively) and sphingomyelins (SM) species (corresponding p-value <0.001 and <0.01), attributed to choline head-group, while other GPL appeared to have opposite traits, indicating a dichotomy of the large family.

There were more ionization preferences that bear fine structural information about the lipids. One example was the loss of water molecule for SPL in the positive mode (FIG. 12) that either involves hydroxyl-group dehydration at the alpha-1 (or alpha-3) position, or cleavage at the same alpha-1 position (FIG. 2a). Similar dehydration can also happen at the glycerol backbone of pPE, lysoPE, lysoPC, DG and MG. In the same manner, the lack of hydroxyl group on the glycerol backbone of TG and other GPL also implied the absence of $[M+H]-H_2O$ species in these cases.

Overall, the capacity to consistently uncover signature product ions hinges on the implementation of both presumptive and m/z screenings, so as to materially benefit from novel discovery and extensive prior knowledge respectively. In doing so, it enables one to shift from limited identification based on expert knowledge, to a more unbiased and global framework. Also, by invariably recovering the most intense features, hybrid screening may allow a more robust differential comparison between samples based on their intensities.

Knowledge of Preferred Product Ions Improves Accuracy of Identification

To demonstrate the importance of incorporating knowledge of preferred product ions, negative-control candidates based on parental mass matching were generated, but with incorrect preferred daughters (score >9.0), followed by validating them. As expected, none of these 47 lipid conjectures could be confirmed by $MS^2$ technique (three had low intensities) (FIG. 13). Furthermore, among them, 26 already have higher-scoring alternatives that were independently affirmed to be correct, and with the expected dominant daughters. The utility of prescribing pre-processing rules on the preferred mode of parent ionization was clearly confirmed.

To elucidate more physical basis on why these negative-controls were false, they were categorized according to their wrongly-associated preferred daughters, and 5 frequent sources of erroneous annotation were found (FIG. 14). Particularly, there were 16 false instances of PC, PE and pPE that incorrectly imply widespread and habitual fatty-acyl fragmentation among the GPL. However, they were not observed as leading features from routine spectra inspection.

Along the same line, there was no evidence of GLS, CL, Cer, and prenols forming the $[M]^+$ precursor species. Similar arguments can be made against other cases, such as [M–H+Na]$^+$ and $[M+2Na-H]^+$ species. Notably, there were 5 false ceramide-phosphates (CerP), all suggested by purported $[M+H]^+$ ($-H_3PO_4$) dominant daughters, but the underlying parents were conclusively determined to be Cer subsequently. It also speaks volume that there is not a single validated lipid with these doubtful preferred daughters (FIG. 15). In contrast, candidates consistent with the understanding of preferred ions had a distinctly larger proportion of true positives (65/73 versus 0/44 in FIG. 13), and just three of them had alternative hypotheses with better scores, in comparison to 26 for those with the wrong lead feature annotation (FIG. 13). Thus, it is essential to discern the identity of the leading spectra feature in order to generate reliable predictions.

Interestingly, there are subtle differences in the preferred daughter profiles, which can be exploited further. Among common product-ions, although there were more $[M+Na]^+$ compared to $[M+H]^+$ species globally (90% vs. 68% in FIG. 11), there was a lower proportion of $[M+Na]^+$ dominant daughters (17/77 vs. 30/77 for $[M+H]^+$ in the pie-chart of FIG. 15). Clearly, dominance should be a part of LC-MS-based signatures.

INDUSTRIAL APPLICABILITY

As can be seen from the previous section including the examples provided, the method or the framework disclosed in the present invention may be useful for analysing and identifying plurality of lipids, in particular when dealing with a large number of datasets since it is impractical to conduct the exhaustive confirmatory analyses. Further, the method or the framework described above may also be used in the event that the prospect of rigorous validation is limited or not immediately available, for example, researchers may need to generate biological hypotheses within a short span of time, while awaiting time-consuming verification. In other situations, additional samples for validation may be unavailable, difficult to replicate, or maintain.

Considering the above, the method or the framework may be potentially useful to be implemented in various sectors including health, medical, pharmaceutical and food industry.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method of identifying a plurality of lipids in a sample that is profiled using a combined Liquid Chromatography-Mass Spectrometry (LC-MS) technique, comprising the steps of:
    a) providing a list of Liquid Chromatography-Mass Spectrometry (LC-MS)-based mass features;
    b) deconvoluting said list of LC-MS-based mass features;
    c) inferring daughter ions from the deconvoluted list of LC-MS-based mass features;
    d) identifying one or more parental exact masses from the inferred daughter ions;
    e) scoring each of the one more parental exact masses based on the inferred daughter ions;
    f) determining characteristic mass features in response to the scoring of each of the one or more parental exact masses; and
    g) determining each of the plurality of lipids based on the characteristic mass features thereof,
    wherein step b) comprises deconvoluting intensity mass features comprising high intensity mass features, low intensity mass features, or combinations thereof in the list of LC-MS-based mass features to separate the LC-MS-based mass features into groups, each of the groups arising from a same lipid specie.

2. The method according to claim 1, further comprising the step of validating the inferred daughter ions and/or the plurality of lipids.

3. The method according to claim 1, wherein step g) comprises reducing false lipid identification of each of the plurality of lipids by deconvoluting the intensity mass features to separate the LC-MS-based mass features into groups, wherein the false lipid identification comprises a false positive, a false negative, or a combination of false positive and false negative.

4. The method according to claim 1, wherein step c) comprises inferring common daughter ions, specific daughter ions or combinations thereof.

5. The method according to claim 1, further comprising the step of preparing the sample comprising the plurality of lipids, prior to step a).

6. The method according to claim 1, wherein deconvoluting the list of LC-MS-based mass features of step b) comprises the steps of:
    b1) providing quality control (QC) samples at regular intervals, wherein the QC samples are selected to be representative of a type of the sample being profiled using the combined LC-MS technique;
    b2) providing a model of intensity drift based on the LC-MS-based mass features in the QC samples; and
    b3) correcting the intensity mass features of said list of LC-MS-based mass features using the model of step b2).

7. The method according to claim 1, wherein deconvoluting the list of LC-MS-based mass features comprises reconstructing individual spectra of each of the plurality of lipids.

8. The method according to claim 7, wherein reconstructing individual spectra of each of the plurality of lipids comprises the step of clustering the LC-MS-based mass features according to locations and intensity profiles along a retention time (RT) dimension to reconstruct the individual spectra.

9. The method according to claim 8, wherein inferring the daughter ions comprises the step of matching mass-to-charge (m/z) values of the reconstructed individual spectra with a database to obtain a list of candidate exact-masses from which the one or more parental exact masses will be extracted.

10. The method according to claim 9, wherein the database comprises an in-source fragment database, a specific adduct database or a combination thereof.

11. The method according to claim 10, wherein inferring the daughter ions further comprises a presumptive screening step to derive a list of preferred ions for each lipid class.

12. The method according to claim 11, wherein the presumptive screening step comprises iteratively assigning individual m/z values in each spectrum with a list of product ions to account for the inferred daughter ions absent in the database.

13. The method according to claim 9, wherein identifying the one or more parental exact masses further comprises the step of grouping all candidate exact masses in the list of candidate exact-masses into one or more groups of candidate exact-masses, each candidate exact-mass within a group having an exact-mass within an average spacing of less than two-times machine resolution of every candidate exact-mass in the group.

14. The method according to claim 11, wherein step e) scoring each of the one or more parental exact masses based on the inferred daughter ions comprises calculating a feature score based on the database m/z matching step and the presumptive screening step.

15. The method according to claim 1, wherein determining each of the plurality of lipids based on characteristic mass features comprises the step of matching unique masses with an organism-specific mass database.

16. The method according to claim 2, wherein validating a lipid of the plurality of lipids comprises confirming that an ion annotation of a most intense mass feature corresponds to one of a preferred product-ion for a lipid class to which the lipid belongs.

17. The method according to claim 2, wherein the step of validating each of the plurality of lipids comprises the step of selecting a lipid with a best parental exact mass score.

18. The method according to claim 2, wherein validating each of the plurality of lipids, comprises identifying each lipid separately using a suitable method.

19. The method according to claim 18, wherein the suitable method is a tandem mass spectroscopy ($MS^2$) technique.

20. Use of a method of identifying a plurality of lipids in a sample that is profiled using a combined Liquid Chromatography-Mass Spectrometry (LC-MS) technique to identify a plurality of lipids undergoing in-source fragmentation, the method of identifying a plurality of lipids in a sample that is profiled using a combined LC-MS technique comprising:
  a) providing a list of LC-MS-based mass features;
  b) deconvoluting said list of LC-MS-based mass features;
  c) inferring daughter ions from the deconvoluted list of LC-MS-based mass features;
  d) identifying one or more parental exact masses from the inferred daughter ions;
  e) scoring each of the one more parental exact masses based on the inferred daughter ions;
  f) determining characteristic mass features in response to the scoring of each of the one or more parental exact masses; and
  g) determining each of the plurality of lipids based on the characteristic mass features thereof,
  wherein step b) comprises deconvoluting intensity mass features comprising high intensity mass features, low intensity mass features, or combinations thereof in the list of LC-MS-based mass features to separate the LC-MS-based mass features into groups, each of the groups arising from a same lipid specie.

21. The method according to claim 1, wherein step c) further comprises independently classifying common daughter ions and specific daughter ions as dominant and non-dominant daughter ions.

22. The method according to claim 6, wherein step b2) comprises performing a regression procedure on the LC-MS-based mass features.

23. The method according to claim 22, wherein step b2) comprises performing the regression procedure on the LC-MS-based intensity mass features of the QC samples.

24. The method according to claim 22, wherein the regression procedure comprises one or more of a linear regression, a non-linear regression, or a 'LOcal regrESSion' (LOESS).

* * * * *